(12) United States Patent
Nyanguile et al.

(10) Patent No.: US 11,299,518 B2
(45) Date of Patent: Apr. 12, 2022

(54) FUSION RESPIRATORY SYNCYTIAL VIRUS INHIBITORS AND USE THEREOF

(71) Applicant: FONDATION THE ARK, Sion (CH)

(72) Inventors: Origene Nyanguile, Grimisuat (CH); Jean-Manuel Segura, Vevey (CH); Dominique Garcin, Chens-Sur-Leman (FR)

(73) Assignee: FONDATION THE ARK, Sion (CH)

( * ) Notice: Subject to any disclaimer, the term of this patent is extended or adjusted under 35 U.S.C. 154(b) by 74 days.

(21) Appl. No.: 16/081,431

(22) PCT Filed: Mar. 2, 2017

(86) PCT No.: PCT/EP2017/054966
§ 371 (c)(1),
(2) Date: Aug. 31, 2018

(87) PCT Pub. No.: WO2017/149098
PCT Pub. Date: Sep. 8, 2017

(65) Prior Publication Data
US 2019/0055291 A1     Feb. 21, 2019

(30) Foreign Application Priority Data
Mar. 3, 2016 (EP) .................................. 16158364

(51) Int. Cl.
| | | |
|---|---|---|
| *C07K 14/135* | (2006.01) | |
| *A61K 39/12* | (2006.01) | |
| *A61P 31/14* | (2006.01) | |
| *A61K 38/16* | (2006.01) | |
| *A61K 38/00* | (2006.01) | |

(52) U.S. Cl.
CPC ............ *C07K 14/135* (2013.01); *A61K 38/16* (2013.01); *A61K 39/12* (2013.01); *A61P 31/14* (2018.01); *A61K 38/00* (2013.01); *C12N 2760/18521* (2013.01); *C12N 2760/18534* (2013.01)

(58) Field of Classification Search
None
See application file for complete search history.

(56) References Cited

U.S. PATENT DOCUMENTS

| | | | | |
|---|---|---|---|---|
| 6,348,568 B1 * | 2/2002 | Barney | ................. | C07K 5/1021 530/300 |
| 2016/0046672 A1 * | 2/2016 | Brown | ............... | C07K 14/4705 530/326 |

FOREIGN PATENT DOCUMENTS

| | | |
|---|---|---|
| WO | WO 2010/148335 | 12/2010 |
| WO | WO 2012/142604 | 10/2012 |
| WO | WO 2013/102211 | 7/2013 |
| WO | WO 2015/135925 | 9/2015 |

OTHER PUBLICATIONS

Andries, K. et al. "Substituted benzimidazoles with nanomolar activity against respiratory syncytial virus" *Antiviral Research*, 2003, pp. 209-219, vol. 60.
Bailly, B. et al. "Targeting human respiratory syncytial virus transcription anti-termination factor M2-1 to inhibit in vivo viral replication" *Scientific Reports*, May 19, 2016, pp. 1-11, vol. 6, No. 25806.
Bird, G. H. et al. "Mucosal delivery of a double-stapled RSV peptide prevents nasopulmonary infection" *The Journal of Clinical Investigation*, May 2014, pp. 2113-2124, vol. 124, No. 5.
Bonfanti, J-F. et al. "Selection of a Respiratory Syncytial Virus Fusion Inhibitor Clinical Candidate. 2. Discovery of a Morpholinopropylaminobenzimidazole Derivative (TMC353121)" *Journal of Medicinal Chemistry*, Feb. 7, 2008, pp. 875-896, vol. 51, No. 4.
Collins, P. L. et al. "Progress in understanding and controlling respiratory syncytial virus: still crazy after all these years" *Virus Research*, Dec. 2011, pp. 1-48, vol. 162, Nos. 1-2.
Detalle, L. et al. "Generation and Characterization of ALX-0171, a Potent Novel Therapeutic Nanobody for the Treatment of Respiratory Syncytial Virus Infection" *Antimicrobial Agents and Chemotherapy*, Jan. 2016, pp. 6-13, vol. 60, No. 1.
Devincenzo, J. P. et al. "Oral GS-5806 Activity in a Respiratory Syncytial Virus Challenge Study" *The New England Journal of Medicine*, Aug. 21, 2014, pp. 711-722, vol. 371, No. 8.
Devincenzo, J. P. et al. "Activity of Oral ALS-008176 in Respiratory Syncytial Virus Challenge Study" *The New England Journal of Medicine*, Nov. 19, 2015, pp. 2048-2058, vol. 373, No. 21.
Gaillard, V. et al. "A Short Double-Stapled Peptide Inhibits Respiratory Syncytial Virus Entry and Spreading" *Antimicrobial Agents and Chemotherapy*, Apr. 2017, pp. 1-19, vol. 61, No. 4.
Geurink, P. P. et al. "Incorporation of Non-natural Amino Acids Improves Cell Permeability and Potency of Specific Inhibitors of Proteasome Trypsin-like Sites" *Journal of Medicinal Chemistry*, Feb. 14, 2013, pp. 1-32, vol. 56, No. 3.
Hall, C. B. et al. "The Burden of Respiratory Syncytial Virus Infection in Young Children" *New England Journal of Medicine*, Feb. 5, 2009, pp. 1-18, vol. 360, No. 6.
Hallak, L. K. et al. "Iduronic Acid-Containing Glycosaminoglycans on Target Cells Are Required for Efficient Respiratory Syncytial Virus Infection" *Virology*, 2000, pp. 264-275, vol. 271.
Hilinski, G. J. et al. "Stitched α-Helical Peptides via Bis Ring-Closing Metathesis" *Journal of the American Chemical Society*, Aug. 8, 2014, pp. 12314-12322, vol. 136, Correction, p. 1.
Jackson, D. Y. et al. "General Approach to the Synthesis of Short α-Helical Peptides" *Journal of the American Chemical Society*, 1991, pp. 9391-9392, vol. 113.
Jordan, R. et al. "Antiviral Efficacy of a respiratory Syncytial Virus (RSV) Fusion Inhibitor in a Bovine Model of RSV Infection" *Antimicrobial Agents and Chemotherapy*, Aug. 2015, pp. 4889-4900, vol. 59, No. 8.
Kim, Y-W. et al. "Synthesis of all-hydrocarbon stapled α-helical peptides by ring-closing olefin metathesis" *Nature Protocols*, 2011, pp. 761-771, vol. 6, No. 6.

(Continued)

*Primary Examiner* — Maury A Audet
(74) *Attorney, Agent, or Firm* — Saliwanchik, Lloyd & Eisenschenk

(57) ABSTRACT

The present invention relates novel peptides useful for the prevention and/or treatment of respiratory syncytial virus (RSV) infections.

13 Claims, 11 Drawing Sheets

Specification includes a Sequence Listing.

(56) References Cited

OTHER PUBLICATIONS

Lambert, D. M. et al. "Peptides from conserved regions of paramyxovirus fusion (F) proteins are potent inhibitors of viral fusion" *PNAS*, Mar. 1996, pp. 2186-2191, vol. 93.

Marsault, E. et al. "Macrocycles Are Great Cycles: Applications, Opportunities, and Challenges of Synthetic Macrocycles in Drug Discovery" *Journal of Medicinal Chemistry*, Mar. 7, 2011, pp. 1961-2004, vol. 54.

Mas-Moruno, C. et al. "Increasing $\alpha v\beta 3$ Selectivity of the Anti-Angiogenic Drug Cilengitide by N-Methylation" *Angewandte Chemie International Edition*, 2011, pp. 9496-9500, vol. 50.

Matthews, J. M. et al. "The Core of the Respiratory Syncytial Virus Fusion Protein Is a Trimeric Coiled Coil" *Journal of Virology*, Jul. 2000, pp. 5911-5920, vol. 74, No. 13.

Mejías, A. et al. "Review of palivizumab in the prophylaxis of respiratory syncytial virus (RSV) in high-risk infants" *Biologics: Targets & Therapy*, 2008, pp. 433-439, vol. 2, No. 3.

Ösapay, G. et al. "Multicyclic Polypeptide Model Compounds. 2. Synthesis and Conformational Properties of a Highly $\alpha$-Helical Uncosapeptide Constrained by Three Side-Chain to Side-Chain Lactam Bridges" *Journal of American Chemical Society*, 1992, pp. 6966-6973, vol. 114.

Park, M. et al. "A Fluorescence Polarization Assay Using an Engineered hRSV F protein as a Direct Screening Platform" *Analytical Biochemistry*, Feb. 15, 2011, pp. 1-23, vol. 409, No. 2.

Porotto, M. et al. "Kinetic Dependence of Paramyxovirus Entry Inhibition" *Journal of Virology*, Jul. 2009, pp. 6947-6951, vol. 83, No. 13.

Rameix-Welti, M-A. et al. "Visualizing the replication of respiratory syncytial virus in cells and in living mice" *Nature Communications*, Oct. 3, 2014, pp. 1-10, vol. 5, No. 5104.

Rand, A. C. et al. "Optimizing PK properties of cyclic peptides: the effect of side chain substitutions on permeability and clearance" *MedChemComm*, 2012, pp. 1282-1289, vol. 3.

Roymans, D. et al. "Binding of a potent small-molecule inhibitor of six-helix bundle formation requires interactions with both heptad-repeats of the RSV fusion protein" *PNAS*, Jan. 5, 2010, pp. 308-313, vol. 107, No. 1.

Roymans, D. et al. "Pneumologie et allergologie Co-19—JNJ-53718678 :un composé actif contre le virus respiratoire syncitial" *Archives de pediatrie*, 2015, p. 215, vol. 22.

Shepherd, N. E. et al. "Modular $\alpha$-Helical Mimetics with Antiviral Activity against Respiratory Syncitial Virus" *Journal of the American Chemical Society*, 2006, pp. 13284-13289, vol. 128.

Spokoyny, A. M. et al. "A Perfluoroaryl-Cysteine $S_NAr$ Chemistry Approach to Unprotected Peptide Stapling" *Journal of the American Chemical Society*, Apr. 24, 2013, pp. 1-10, vol. 135, No. 16.

Origene, N. "Discovery of Short Stapled Peptides, Inhibitors of RSV Fusion" Oral Presentation, 10th International Respiratory Syncytial Virus Symposium, Sep. 28-Oct. 1, 2016, Bariloche, Patagonia, Argentina. LLA LLAO Hotel, pp. 1-6.

Tayyari, F. et al. "Identification of nucleolin as a cellular receptor for human respiratory syncytial virus" *Nature Medicine*, Sep. 2011, pp. 1132-1135; Online methods p. 1, vol. 17, No. 9.

Thompson, W. W. et al. "Mortality Associated With Influenza and Respiratory Syncytial Virus in the United States" *JAMA*, Jan. 8, 2003, pp. 179-186, vol. 289, No. 2.

Verdine, G. L. et al. "Stapled Peptides for Intracellular Drug Targets" *Methods in Enzymology*, 2012, pp. 3-33, vol. 503.

Walensky, L. D. et al. "Hydrocarbon-Stapled Peptides: Principles, Practice, and Progress" *Journal of Medicinal Chemistry*, Feb. 19, 2014, pp. 6275-6288, vol. 57.

White, C. J. et al. "Contemporary strategies for peptide macrocyclization" *Nature Chemistry*, Jul. 2011, pp. 509-524, vol. 3.

Yu, C. et al. "Synthesis and Study of Peptides with Semirigid i and i+7 Side-chain Bridges Designed for $\alpha$-Helix Stabilization" *Bioorganic & Medicinal Chemistry*, 1999, pp. 161-175, vol. 7.

Yu, K-L. et al. "Respiratory syncytial virus fusion inhibitors. Part 3: Water-soluble benzimidazol-2-one derivatives with antiviral activity in vivo" *Bioorganic & Medicinal Chemistry*, 2006, pp. 1115-1122, vol. 16.

Yu, K-L. et al. "Respiratory syncytial virus fusion inhibitors. Part 4: Optimization for oral bioavailability" *Bioorganic & Medicinal Chemistry Letters*, 2007, pp. 895-901, vol. 17.

Yunus, A. S. et al. "Elevated Temperature Triggers Human Respiratory Syncytial Virus F Protein Six-Helix Bundle Formation" *Virology*, Jan. 20, 2010, pp. 1-30, vol. 396, No. 2.

Zhao, X. et al. "Structural characterization of the human respiratory syncytial virus fusion protein core" *PNAS*, Dec. 19, 2000, pp. 14172-14177, vol. 97, No. 26.

Written Opinion in International Application No. PCT/EP2017/054966, dated Jun. 2, 2017, pp. 1-7.

\* cited by examiner

Figure 1

C6
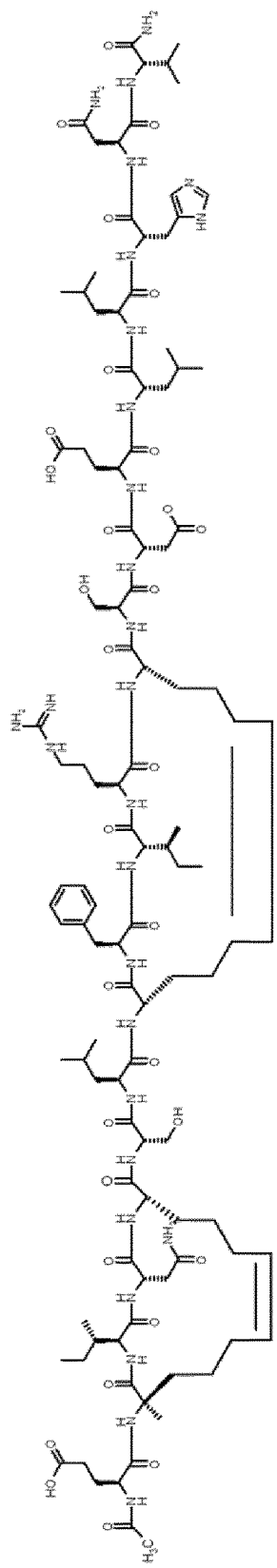
C7
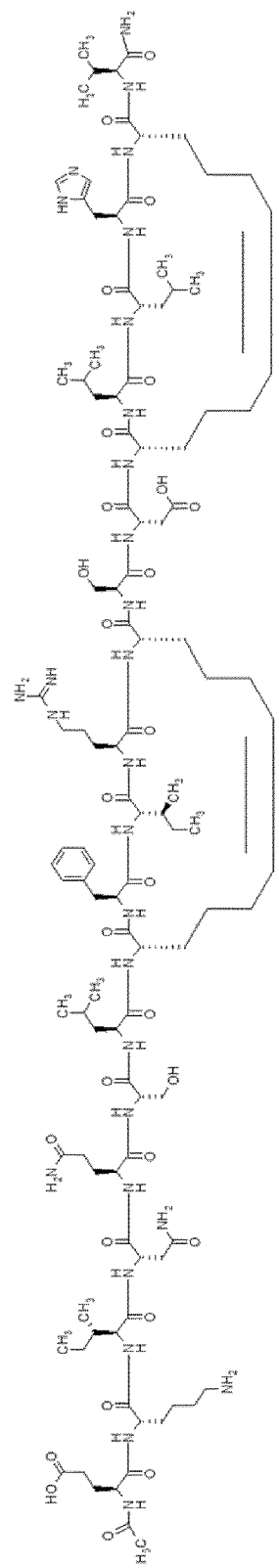
Figure 1 (continued)

Table 2

| Peptides of the invention | Sequence | SEQ ID NO: |
|---|---|---|
| Consensus | Xaa1Xaa2Xaa3Xaa4Xaa5Xaa6Xaa7Xaa8Xaa9Xaa10Xaa11Xaa12Xaa13Xaa14Xaa15Xaa16Xaa17Xaa18Xaa19Xaa20 | 1 |
| 4bb cons | SEQ ID NO:1 wherein $X_{aa4}$, $X_{aa8}$, $X_{aa11}$ and $X_{aa15}$ are each independently a cross-linked amino-acid | 2 |
| 4bb spe | E K I Xaa4 Q S L $X_{aa8}$ F I $X_{aa11}$ K S D $X_{aa15}$ L L H N V wherein $X_{aa4}$, $X_{aa8}$, $X_{aa11}$ and $X_{aa15}$ are each independently a cross-linked amino-acid | 3 |
| 4bb | E K I Xaa4 Q S L $X_{aa8}$ F I $X_{aa11}$ K S D $X_{aa15}$ L L H N V wherein $X_{aa4}$, $X_{aa8}$, $X_{aa11}$ and $X_{aa15}$ are (S)-2-(4-pentenyl)alanine or (S)-2-(4-pentenyl)glycine and N-term acetylated and C-term amidated | 35 |
| V4bb497 | SEQ ID NO:3 wherein $E_1$ is replaced by A, $X_{aa4}$, $X_{aa8}$, $X_{aa11}$ and $X_{aa15}$ are (S)-2-(4-pentenyl)alanine and N-term acetylated and C-term amidated | 4 |
| V4bb498 | SEQ ID NO:3 wherein $K_2$ is replaced by A, $X_{aa4}$, $X_{aa8}$, $X_{aa11}$ and $X_{aa15}$ are (S)-2-(4-pentenyl)alanine and N-term acetylated and C-term amidated | 5 |
| V4bb499 | SEQ ID NO:3 wherein $I_3$ is replaced by A, $X_{aa4}$, $X_{aa8}$, $X_{aa11}$ and $X_{aa15}$ are (S)-2-(4-pentenyl)alanine and N-term acetylated and C-term amidated | 6 |
| V4bb501 | SEQ ID NO:3 wherein $Q_5$ is replaced by A, $X_{aa4}$, $X_{aa8}$, $X_{aa11}$ and $X_{aa15}$ are (S)-2-(4-pentenyl)alanine and N-term acetylated and C-term amidated | 8 |
| V4bb502 | SEQ ID NO:3 wherein $S_6$ is replaced by A, $X_{aa4}$, $X_{aa8}$, $X_{aa11}$ and $X_{aa15}$ are (S)-2-(4-pentenyl)alanine and N-term acetylated and C-term amidated | 9 |
| V4bb503 | SEQ ID NO:3 wherein $L_7$ is replaced by A, $X_{aa4}$, $X_{aa8}$, $X_{aa11}$ and $X_{aa15}$ are (S)-2-(4-pentenyl)alanine and N-term acetylated and C-term amidated | 10 |
| V4bb505 | SEQ ID NO:3 wherein $F_9$ is replaced by A, $X_{aa4}$, $X_{aa8}$, $X_{aa11}$ and $X_{aa15}$ are (S)-2-(4-pentenyl)alanine and N-term acetylated and C-term amidated | 11 |
| V4bb510 | SEQ ID NO:3 wherein $D_{14}$ is replaced by A, $X_{aa4}$, $X_{aa8}$, $X_{aa11}$ and $X_{aa15}$ are (S)-2-(4-pentenyl)alanine and N-term acetylated and C-term amidated | 12 |

Figure 2

Table 2 continued

| Peptides of the invention | Sequence | SEQ ID NO: |
|---|---|---|
| V4bb512 | SEQ ID NO:3 wherein $L_{16}$ is replaced by A, $X_{aa4}$, $X_{aa8}$, $X_{aa11}$ and $X_{aa15}$ are (S)-2-(4-pentenyl)alanine, N-term acetylated and C-term amidated | 13 |
| V4bb514 | SEQ ID NO:3 wherein $H_{18}$ is replaced by A, $X_{aa4}$, $X_{aa8}$, $X_{aa11}$ and $X_{aa15}$ are (S)-2-(4-pentenyl)alanine, N-term acetylated and C-term amidated | 14 |
| V4bb515 | SEQ ID NO:3 wherein $N_{19}$ is replaced by A, $X_{aa4}$, $X_{aa8}$, $X_{aa11}$ and $X_{aa15}$ are (S)-2-(4-pentenyl)alanine, N-term acetylated and C-term amidated | 15 |
| V4bb516 | SEQ ID NO:3 wherein $V_{20}$ is replaced by A, $X_{aa4}$, $X_{aa8}$, $X_{aa11}$ and $X_{aa15}$ are (S)-2-(4-pentenyl)alanine, N-term acetylated and C-term amidated | 16 |
| 4ca cons | SEQ ID NO:1 wherein $X_{aa2}$, $X_{aa5}$, $X_{aa8}$, $X_{aa12}$ are each independently a cross-linked amino-acid | 17 |
| 4ca spe | E $X_{aa2}$ I N $X_{aa5}$ S L $X_{aa8}$ F I R $X_{aa12}$ S D E L L H N V wherein $X_{aa2}$, $X_{aa5}$, $X_{aa8}$, $X_{aa12}$ are each independently a cross-linked amino-acid | 18 |
| 4ca | E $X_{aa2}$ I N $X_{aa5}$ S L $X_{aa8}$ F I R $X_{aa12}$ S D E L L H N V wherein $X_{aa2}$ is (R)-2-(4-pentenyl)alanine and $X_{aa5}$, $X_{aa8}$, $X_{aa12}$ are (S)-2-(4-pentenyl)alanine, N-term acetylated and C-term amidated | 36 |
| V4ca511 | SEQ ID NO:18 wherein E15 is replaced by A, wherein $X_{aa2}$ is (R)-2-(4-pentenyl)alanine and $X_{aa5}$, $X_{aa8}$, $X_{aa12}$ are (S)-2-(4-pentenyl)alanine, N-term acetylated and C-term amidated | 37 |
| 4ca13 | SEQ ID NO:36 wherein $N_{19}$ and $V_{20}$ are deleted, N-term acetylated and C-term amidated | 38 |
| 4ca16 | SEQ ID NO:36 wherein $E_1$, $H_{18}$, $N_{19}$ and $V_{20}$ are deleted, N-term acetylated and C-term amidated | 39 |
| 4ca-var1 | SEQ ID NO:36 wherein $L_7$ is replaced by L-3-tButyl-Alanine, N-term acetylated and C-term amidated | 40 |
| 4ca-var2 | SEQ ID NO:36 wherein $L_7$ is replaced by L-2-Cyclopentyl-Glycine, N-term acetylated and C-term amidated | 41 |
| 4ca-var3 | SEQ ID NO: 36 wherein $L_7$ is replaced by 2-Cyclohexyl-L-Glycine, N-term acetylated and C-term amidated | 42 |
| 4ca-var4 | SEQ ID NO: 36 wherein $L_{16}$ is replaced by L-3-tButyl-Alanine, N-term acetylated and C-term amidated | 43 |
| 4ca-var5 | SEQ ID NO: 36 wherein $N_4$ is replaced by K, $L_{16}$ is replaced by L-3-tButyl-Alanine, N-term acetylated and C-term amidated | 44 |
| 4ca-var6 | SEQ ID NO: 36 wherein $N_4$ is replaced by R, $L_{16}$ is replaced by L-3-tButyl-Alanine, N-term acetylated and C-term amidated | 45 |
| 4ca-var7 | SEQ ID NO: 36 wherein $L_{16}$ is replaced by 3-Cyclohexyl-L-Alanine, N-term acetylated and C-term amidated | 46 |
| 4ca-var8 | SEQ ID NO: 36 wherein $L_{16}$ is replaced by L-3-tButyl-Alanine, $H_{19}$ and $V_{20}$ are deleted, N-term acetylated and C-term amidated | 47 |
| 4ca-var9 | SEQ ID NO: 36 wherein $L_{16}$ and $L_{17}$ are replaced by L-3-tButyl-Alanine, N-term acetylated and C-term amidated | 48 |

Figure 2 (continued)

Table 2 continued

| Peptides of the invention | Sequence | SEQ ID NO: |
|---|---|---|
| 4ca2 | E Xaa2 I N $X_{aa5}$ S L $X_{aa8}$ F I R $X_{aa12}$ S D E L L H N V wherein $X_{aa3}$ is (R)-2-(4-pentenyl)alanine and $X_{aa5}$, $X_{aa8}$, $X_{aa12}$ are (S)-2-(4-pentenyl)glycine, N-term acetylated and C-term amidated | 49 |
| 4a cons | SEQ ID NO: 1 wherein $X_{aa8}$, $X_{aa12}$, $X_{aa15}$ and $X_{aa19}$ are each independently a cross-linked amino-acid | 33 |
| 4a spe | E K I N Q S L $X_{aa8}$ F I R $X_{aa12}$ S D $X_{aa15}$ L L H$X_{aa19}$ V wherein $X_{aa8}$, $X_{aa12}$, $X_{aa15}$ and $X_{aa19}$ are each independently a cross-linked amino-acid | 34 |
| 4a | E K I N Q S L $X_{aa8}$ F I R $X_{aa12}$ S D $X_{aa15}$ L L H$X_{aa19}$ V wherein $X_{aa8}$, $X_{aa12}$, $X_{aa15}$ and $X_{aa19}$ are (S)-2-(4-pentenyl)alanine, N-term acetylated and C-term amidated | 19 |
| 4a2 | E K I N Q S L $X_{aa8}$ F I R $X_{aa12}$ S D $X_{aa15}$ L L H$X_{aa19}$ V wherein $X_{aa8}$, $X_{aa12}$, $X_{aa15}$ and $X_{aa19}$ are (S)-2-(4-pentenyl)glycine, N-term acetylated and C-term amidated | 50 |
| V4a$_{500}$ | SEQ ID NO:19 wherein N4 is replaced by A, wherein $X_{aa8}$, $X_{aa12}$, $X_{aa15}$ and $X_{aa19}$ are (S)-2-(4-pentenyl)alanine, N-term acetylated and C-term amidated | 7 |
| 3ac | E Q S L $X_{504}$ F I R $X_{508}$ S D $X_{511}$ L L H$X_{515}$ V wherein $X_{504}$, $X_{508}$, $X_{511}$ and $X_{515}$ are (S)-2-(4-pentenyl)alanine, N-term acetylated and C-term amidated | 20 |

Figure 2 (continued)

Table 2 continued

| Comparative Peptides | Sequence | SEQ ID NO.: |
|---|---|---|
| 4 | E K I N Q S L A F I R K S D E L L H N V | 22 |
| 4e | E K I N Q S L $8_{504}$ F I R K S D $X_{511}$ L L H N V wherein $8_{504}$ is (R)-2-(7-octenyl)alanine, $X_{511}$ is (S)-2-(4-pentenyl)alanine and N-term acetylated and C-term amidated | 23 |
| 4ef | $8_{497}$ K I N Q S L $X_{504}$ F I R $8_{508}$ S D E L L H $X_{515}$ V wherein $8_{497}$ and $8_{508}$ are (R)-2-(7-octenyl)alanine, $X_{504}$ and $X_{515}$ are (S)-2-(4-pentenyl)alanine and N-term acetylated and C-term amidated | 30 |
| 4bf | E K I $X_{500}$ Q S L $X_{504}$ F I R $8_{508}$ S D E L L H $X_{515}$ V wherein $X_{500}$, $X_{504}$ and $X_{515}$ are (S)-2-(4-pentenyl)alanine, $8_{508}$ is (R)-2-(7-octenyl)alanine, and N-term acetylated and C-term amidated | 21 |

Figure 2 (continued)

Table 3

| Comparative Peptides | Sequence |
|---|---|
| HR2 SEQ ID NO: 24 | $N_{476}$FY DPLV FPS D EF DA S IS QVN E KIN QSL A FIR K SDE LLHN VNAGKSTN$_{524}$ |
| X-ray SEQ ID NO: 25 | $P_{480}$LV FPS D EF DA S IS QVN E KIN QSL A FIR K SDE LLHN VN$_{516}$ |
| T108 SEQ ID NO: 26 | $Y_{473}$DPLV FPS D EF DA SI S QVN E KIN QSL A FIR K SDE L$_{512}$ |
| T118 SEQ ID NO: 27 | $F_{483}$DA SI s QVN E KIN QSL A FIR K SDE LLHN VNAGKST$_{522}$ |
| 1eg SEQ ID NO: 29 | EFPS $X_{86}$EF D$X_{490}$SI$X_{493}$QVN$X_{497}$KIN wherein $X_{486}$, $X_{490}$, $X_{493}$ and $X_{497}$ are (S)-2-(4-pentenyl)alanine and N-term acetylated and C-term amidated |
| 3 SEQ ID NO: 31 | EQ$_{501}$SLA FIR K SDE LLHN V$_{516}$ |
| 3a SEQ ID NO: 32 | EQ$_{501}$SL$X_{504}$FIR $X_{508}$SDE LLHN V$_{516}$ wherein $X_{504}$ and $X_{508}$ are (S)-2-(4-pentenyl)alanine and N-term acetylated and C-term amidated |
| SAFH-RSVF$_{BD}$ SEQ ID NO: 28 | $F_{483}$D8$_{490}$ SIS QVN $X_{497}$KIN QSLA FI8$_{507}$K SDE LL $X_{514}$ NVNAGKST$_{522}$ wherein 8$_{490}$ and 8$_{507}$ are (R)-2-(7-octenyl)alanine, $X_{497}$ and $X_{514}$ (S)-2-(4-pentenyl)alanine and N-term acetylated and C-term amidated |

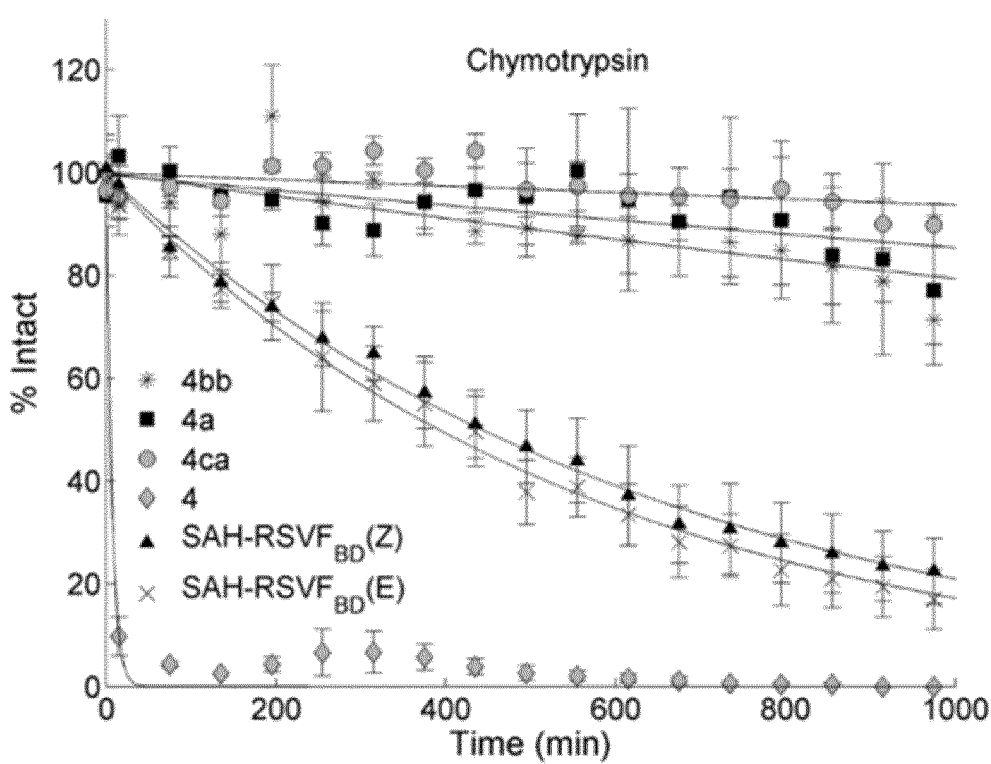
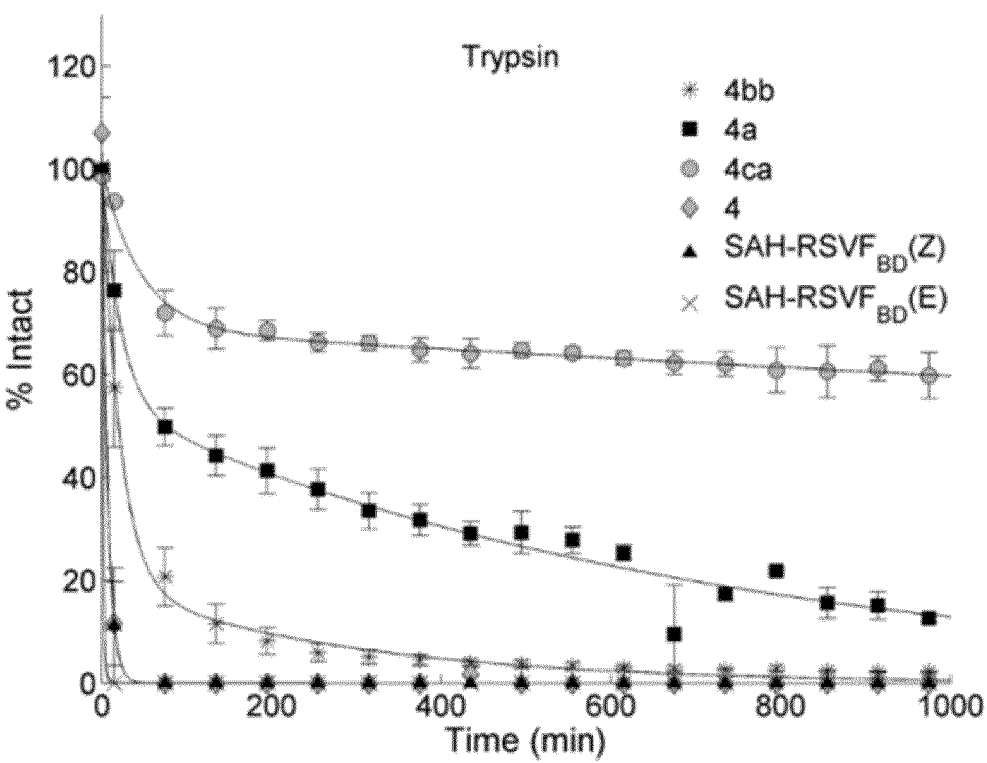
Figure 3 (continued)

SEQUENCE LISTING

```
<160> NUMBER OF SEQ ID NOS: 50

<210> SEQ ID NO 1
<211> LENGTH: 20
<212> TYPE: PRT
<213> ORGANISM: Artificial Sequence
<220> FEATURE:
<223> OTHER INFORMATION: Consensus
<220> FEATURE:
<221> NAME/KEY: MISC_FEATURE
<222> LOCATION: (1)..(1)
<223> OTHER INFORMATION: Any amino acid
<220> FEATURE:
<221> NAME/KEY: MISC_FEATURE
<222> LOCATION: (2)..(2)
<223> OTHER INFORMATION: selected from any amino acid or a cross-linked
      amino-acid
<220> FEATURE:
<221> NAME/KEY: MISC_FEATURE
<222> LOCATION: (3)..(3)
<223> OTHER INFORMATION: apolar amino-acid
<220> FEATURE:
<221> NAME/KEY: MISC_FEATURE
<222> LOCATION: (4)..(4)
<223> OTHER INFORMATION: selected from any amino acid or a cross-linked
      amino-acid
<220> FEATURE:
<221> NAME/KEY: MISC_FEATURE
<222> LOCATION: (5)..(5)
<223> OTHER INFORMATION: selected from any amino acid or a cross-linked
      amino-acid
<220> FEATURE:
<221> NAME/KEY: MISC_FEATURE
<222> LOCATION: (6)..(6)
<223> OTHER INFORMATION: Any amino acid
<220> FEATURE:
<221> NAME/KEY: MISC_FEATURE
<222> LOCATION: (7)..(7)
<223> OTHER INFORMATION: apolar amino-acid
<220> FEATURE:
<221> NAME/KEY: MISC_FEATURE
<222> LOCATION: (8)..(8)
<223> OTHER INFORMATION: cross-linked amino-acid
<220> FEATURE:
<221> NAME/KEY: MISC_FEATURE
<222> LOCATION: (9)..(9)
<223> OTHER INFORMATION: apolar amino-acid
<220> FEATURE:
<221> NAME/KEY: MISC_FEATURE
<222> LOCATION: (10)..(10)
<223> OTHER INFORMATION: apolar amino-acid
<220> FEATURE:
<221> NAME/KEY: MISC_FEATURE
<222> LOCATION: (11)..(12)
```

```
<223> OTHER INFORMATION: independently selected from a polar amino acid
      and a cross-linked amino-acid
<220> FEATURE:
<221> NAME/KEY: MISC_FEATURE
<222> LOCATION: (13)..(13)
<223> OTHER INFORMATION: Serine
<220> FEATURE:
<221> NAME/KEY: MISC_FEATURE
<222> LOCATION: (14)..(14)
<223> OTHER INFORMATION: Any amino acid
<220> FEATURE:
<221> NAME/KEY: MISC_FEATURE
<222> LOCATION: (15)..(15)
<223> OTHER INFORMATION: selected from a polar amino acid and a
      cross-linked amino-acid
<220> FEATURE:
<221> NAME/KEY: MISC_FEATURE
<222> LOCATION: (16)..(16)
<223> OTHER INFORMATION: apolar amino-acid
<220> FEATURE:
<221> NAME/KEY: MISC_FEATURE
<222> LOCATION: (17)..(17)
<223> OTHER INFORMATION: apolar amino-acid
<220> FEATURE:
<221> NAME/KEY: MISC_FEATURE
<222> LOCATION: (18)..(18)
<223> OTHER INFORMATION: Any amino acid
<220> FEATURE:
<221> NAME/KEY: MISC_FEATURE
<222> LOCATION: (19)..(19)
<223> OTHER INFORMATION: selected from any amino acid or a cross-linked
      amino-acid
<220> FEATURE:
<221> NAME/KEY: MISC_FEATURE
<222> LOCATION: (20)..(20)
<223> OTHER INFORMATION: apolar amino-acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 2
<211> LENGTH: 20
<212> TYPE: PRT
<213> ORGANISM: Artificial sequence
<220> FEATURE:
<223> OTHER INFORMATION: Consensus for 4bb
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: apolar amino acid
<220> FEATURE:
<221> NAME/KEY: MISC_FEATURE
<222> LOCATION: (4)..(4)
<223> OTHER INFORMATION: cross-linked amino-acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
```

```
<223> OTHER INFORMATION: apolar amino acid
<220> FEATURE:
<221> NAME/KEY: MISC_FEATURE
<222> LOCATION: (8)..(8)
<223> OTHER INFORMATION: cross linked amino acid
<220> FEATURE:
<221> NAME/KEY: MISC_FEATURE
<222> LOCATION: (9)..(9)
<223> OTHER INFORMATION: apolar amino acid
<220> FEATURE:
<221> NAME/KEY: MISC_FEATURE
<222> LOCATION: (10)..(10)
<223> OTHER INFORMATION: apolar amino acid
<220> FEATURE:
<221> NAME/KEY: MISC_FEATURE
<222> LOCATION: (11)..(11)
<223> OTHER INFORMATION: cross-linked amino-acid
<220> FEATURE:
<221> NAME/KEY: MISC_FEATURE
<222> LOCATION: (12)..(12)
<223> OTHER INFORMATION: polar amino acid
<220> FEATURE:
<221> NAME/KEY: MISC_FEATURE
<222> LOCATION: (13)..(13)
<223> OTHER INFORMATION: Serine
<220> FEATURE:
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(15)
<223> OTHER INFORMATION: cross-linked amino-acid
<220> FEATURE:
<221> NAME/KEY: MISC_FEATURE
<222> LOCATION: (16)..(16)
<223> OTHER INFORMATION: apolar amino acid
<220> FEATURE:
<221> NAME/KEY: MISC_FEATURE
<222> LOCATION: (17)..(17)
<223> OTHER INFORMATION: apolar amino acid
<220> FEATURE:
<221> NAME/KEY: MISC_FEATURE
<222> LOCATION: (18)..(18)
<223> OTHER INFORMATION: any amino acid
<220> FEATURE:
<221> NAME/KEY: MISC_FEATURE
<222> LOCATION: (19)..(19)
<223> OTHER INFORMATION: any amino acid
<220> FEATURE:
<221> NAME/KEY: MISC_FEATURE
<222> LOCATION: (20)..(20)
<223> OTHER INFORMATION: apolar amino acid

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 3
<211> LENGTH: 20
<212> TYPE: PRT
<213> ORGANISM: Artificial sequence
<220> FEATURE:
<223> OTHER INFORMATION: 4bb spe
<220> FEATURE:
<221> NAME/KEY: MISC_FEATURE
<222> LOCATION: (4)..(4)
<223> OTHER INFORMATION: cross-linked amino-acid
<220> FEATURE:
<221> NAME/KEY: MISC_FEATURE
<222> LOCATION: (8)..(8)
<223> OTHER INFORMATION: cross-linked amino-acid
<220> FEATURE:
<221> NAME/KEY: MISC_FEATURE
```

```
<222> LOCATION: (11)..(11)
<223> OTHER INFORMATION: cross-linked amino-acid
<220> FEATURE:
<221> NAME/KEY: MISC_FEATURE
<222> LOCATION: (15)..(15)
<223> OTHER INFORMATION: cross-linked amino-acid

<400> SEQUENCE: 3

Glu Lys Ile Xaa Gln Ser Leu Xaa Phe Ile Xaa Lys Ser Asp Xaa Leu
1               5                   10                  15

Leu His Asn Val
            20

<210> SEQ ID NO 4
<211> LENGTH: 20
<212> TYPE: PRT
<213> ORGANISM: Artificial sequence
<220> FEATURE:
<223> OTHER INFORMATION: V4bb497
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 4

Ala Lys Ile Xaa Gln Ser Leu Xaa Phe Ile Xaa Lys Ser Asp Xaa Leu
1               5                   10                  15

Leu His Asn Val
            20

<210> SEQ ID NO 5
<211> LENGTH: 20
<212> TYPE: PRT
<213> ORGANISM: Artificial sequence
<220> FEATURE:
<223> OTHER INFORMATION: V4bb498
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
```

```
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 5

Glu Ala Ile Xaa Gln Ser Leu Xaa Phe Ile Xaa Lys Ser Asp Xaa Leu
1               5                   10                  15

Leu His Asn Val
            20

<210> SEQ ID NO 6
<211> LENGTH: 20
<212> TYPE: PRT
<213> ORGANISM: Artificial sequence
<220> FEATURE:
<223> OTHER INFORMATION: V4bb499
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 6

Glu Lys Ala Xaa Gln Ser Leu Xaa Phe Ile Xaa Lys Ser Asp Xaa Leu
1               5                   10                  15

Leu His Asn Val
            20

<210> SEQ ID NO 7
<211> LENGTH: 20
<212> TYPE: PRT
<213> ORGANISM: Artificial sequence
<220> FEATURE:
<223> OTHER INFORMATION: V4a500
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
```

-continued

```
<220> FEATURE:
<221> NAME/KEY: MISC_FEATURE
<222> LOCATION: (19)..(19)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 7

Glu Lys Ile Ala Gln Ser Leu Xaa Phe Ile Arg Xaa Ser Asp Xaa Leu
1               5                   10                  15

Leu His Xaa Val
            20

<210> SEQ ID NO 8
<211> LENGTH: 20
<212> TYPE: PRT
<213> ORGANISM: Artificial sequence
<220> FEATURE:
<223> OTHER INFORMATION: V4bb501
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 8

Glu Lys Ile Xaa Ala Ser Leu Xaa Phe Ile Xaa Lys Ser Asp Xaa Leu
1               5                   10                  15

Leu His Asn Val
            20

<210> SEQ ID NO 9
<211> LENGTH: 20
<212> TYPE: PRT
<213> ORGANISM: Artificial sequence
<220> FEATURE:
<223> OTHER INFORMATION: V4bb502
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
```

```
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 9

Glu Lys Ile Xaa Gln Ala Leu Xaa Phe Ile Xaa Lys Ser Asp Xaa Leu
1               5                   10                  15

Leu His Asn Val
            20

<210> SEQ ID NO 10
<211> LENGTH: 20
<212> TYPE: PRT
<213> ORGANISM: Artificial sequence
<220> FEATURE:
<223> OTHER INFORMATION: V4bb503
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 10

Glu Lys Ile Xaa Gln Ser Ala Xaa Phe Ile Xaa Lys Ser Asp Xaa Leu
1               5                   10                  15

Leu His Asn Val
            20

<210> SEQ ID NO 11
<211> LENGTH: 20
<212> TYPE: PRT
<213> ORGANISM: Artificial sequence
<220> FEATURE:
<223> OTHER INFORMATION: V4bb505
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
```

```
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 11

Glu Lys Ile Xaa Gln Ser Leu Xaa Ala Ile Xaa Lys Ser Asp Xaa Leu
1               5                   10                  15

Leu His Asn Val
            20

<210> SEQ ID NO 12
<211> LENGTH: 20
<212> TYPE: PRT
<213> ORGANISM: Artificial sequence
<220> FEATURE:
<223> OTHER INFORMATION: V4bb510
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 12

Glu Lys Ile Xaa Gln Ser Leu Xaa Phe Ile Xaa Lys Ser Ala Xaa Leu
1               5                   10                  15

Leu His Asn Val
            20

<210> SEQ ID NO 13
<211> LENGTH: 20
<212> TYPE: PRT
<213> ORGANISM: Artificial sequence
<220> FEATURE:
<223> OTHER INFORMATION: V4bb512
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
```

```
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 13

Glu Lys Ile Xaa Gln Ser Leu Xaa Phe Ile Xaa Lys Ser Asp Xaa Ala
1               5                   10                  15

Leu His Asn Val
            20

<210> SEQ ID NO 14
<211> LENGTH: 20
<212> TYPE: PRT
<213> ORGANISM: Artificial sequence
<220> FEATURE:
<223> OTHER INFORMATION: V4bb514
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 14

Glu Lys Ile Xaa Gln Ser Leu Xaa Phe Ile Xaa Lys Ser Asp Xaa Leu
1               5                   10                  15

Leu Ala Asn Val
            20

<210> SEQ ID NO 15
<211> LENGTH: 20
<212> TYPE: PRT
<213> ORGANISM: Artificial sequence
<220> FEATURE:
<223> OTHER INFORMATION: V4bb515
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
```

```
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 15

Glu Lys Ile Xaa Gln Ser Leu Xaa Phe Ile Xaa Lys Ser Asp Xaa Leu
1               5                   10                  15

Leu His Ala Val
            20

<210> SEQ ID NO 16
<211> LENGTH: 20
<212> TYPE: PRT
<213> ORGANISM: Artificial sequence
<220> FEATURE:
<223> OTHER INFORMATION: V4bb516
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 16

Glu Lys Ile Xaa Gln Ser Leu Xaa Phe Ile Xaa Lys Ser Asp Xaa Leu
1               5                   10                  15

Leu His Asn Ala
            20

<210> SEQ ID NO 17
<211> LENGTH: 20
<212> TYPE: PRT
<213> ORGANISM: Artificial sequence
<220> FEATURE:
<223> OTHER INFORMATION: Consensus for 4ca
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (2)..(2)
<223> OTHER INFORMATION: cross-linked amino-acid
<220> FEATURE:
<221> NAME/KEY: MISC_FEATURE
<222> LOCATION: (3)..(3)
```

```
<223> OTHER INFORMATION: apolar amino acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: cross-linked amino-acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: apolar amino acid
<220> FEATURE:
<221> NAME/KEY: MISC_FEATURE
<222> LOCATION: (8)..(8)
<223> OTHER INFORMATION: cross-linked amino-acid
<220> FEATURE:
<221> NAME/KEY: MISC_FEATURE
<222> LOCATION: (9)..(9)
<223> OTHER INFORMATION: apolar amino acid
<220> FEATURE:
<221> NAME/KEY: MISC_FEATURE
<222> LOCATION: (10)..(10)
<223> OTHER INFORMATION: apolar amino acid
<220> FEATURE:
<221> NAME/KEY: MISC_FEATURE
<222> LOCATION: (11)..(11)
<223> OTHER INFORMATION: polar amino acid
<220> FEATURE:
<221> NAME/KEY: MISC_FEATURE
<222> LOCATION: (12)..(12)
<223> OTHER INFORMATION: cross-linked amino-acid
<220> FEATURE:
<221> NAME/KEY: MISC_FEATURE
<222> LOCATION: (13)..(13)
<223> OTHER INFORMATION: Serine
<220> FEATURE:
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(15)
<223> OTHER INFORMATION: polar amino acid
<220> FEATURE:
<221> NAME/KEY: MISC_FEATURE
<222> LOCATION: (16)..(16)
<223> OTHER INFORMATION: apolar amino acid
<220> FEATURE:
<221> NAME/KEY: MISC_FEATURE
<222> LOCATION: (17)..(17)
<223> OTHER INFORMATION: apolar amino acid
<220> FEATURE:
<221> NAME/KEY: MISC_FEATURE
<222> LOCATION: (18)..(18)
<223> OTHER INFORMATION: any amino acid
<220> FEATURE:
<221> NAME/KEY: MISC_FEATURE
<222> LOCATION: (19)..(19)
<223> OTHER INFORMATION: any amino acid
<220> FEATURE:
<221> NAME/KEY: MISC_FEATURE
<222> LOCATION: (20)..(20)
<223> OTHER INFORMATION: apolar amino acid

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20
```

-continued

```
<210> SEQ ID NO 18
<211> LENGTH: 20
<212> TYPE: PRT
<213> ORGANISM: Artificial sequence
<220> FEATURE:
<223> OTHER INFORMATION: 4ca specific varied on staples
<220> FEATURE:
<221> NAME/KEY: MISC_FEATURE
<222> LOCATION: (2)..(2)
<223> OTHER INFORMATION: cross-linked amino-acid
<220> FEATURE:
<221> NAME/KEY: MISC_FEATURE
<222> LOCATION: (5)..(5)
<223> OTHER INFORMATION: cross-linked amino-acid
<220> FEATURE:
<221> NAME/KEY: MISC_FEATURE
<222> LOCATION: (8)..(8)
<223> OTHER INFORMATION: cross-linked amino-acid
<220> FEATURE:
<221> NAME/KEY: MISC_FEATURE
<222> LOCATION: (12)..(12)
<223> OTHER INFORMATION: cross-linked amino-acid

<400> SEQUENCE: 18

Glu Xaa Ile Asn Xaa Ser Leu Xaa Phe Ile Arg Xaa Ser Asp Glu Leu
1               5                   10                  15

Leu His Asn Val
            20

<210> SEQ ID NO 19
<211> LENGTH: 20
<212> TYPE: PRT
<213> ORGANISM: Artificial sequence
<220> FEATURE:
<223> OTHER INFORMATION: Peptide 4a
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (19)..(19)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 19

Glu Lys Ile Asn Gln Ser Leu Xaa Phe Ile Arg Xaa Ser Asp Xaa Leu
1               5                   10                  15

Leu His Xaa Val
            20

<210> SEQ ID NO 20
<211> LENGTH: 17
<212> TYPE: PRT
<213> ORGANISM: Artificial sequence
<220> FEATURE:
<223> OTHER INFORMATION: Peptide 3ac
<220> FEATURE:
```

```
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (9)..(9)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: (S)-2-(4-pentenyl)alanine
<220> FEATURE:
<221> NAME/KEY: MISC_FEATURE
<222> LOCATION: (17)..(17)
<223> OTHER INFORMATION: C-term amidated

<400> SEQUENCE: 20

Glu Gln Ser Leu Xaa Phe Ile Arg Xaa Ser Asp Xaa Leu Leu His Xaa
1               5                   10                  15

Val

<210> SEQ ID NO 21
<211> LENGTH: 20
<212> TYPE: PRT
<213> ORGANISM: Artificial sequence
<220> FEATURE:
<223> OTHER INFORMATION: comparative peptide 4bf
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (R)-2-(7-octenyl)alanine
<220> FEATURE:
<221> NAME/KEY: MISC_FEATURE
<222> LOCATION: (19)..(19)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 21

Glu Lys Ile Xaa Gln Ser Leu Xaa Phe Ile Arg Xaa Ser Asp Glu Leu
1               5                   10                  15

Leu His Xaa Val
            20

<210> SEQ ID NO 22
<211> LENGTH: 20
<212> TYPE: PRT
<213> ORGANISM: Artificial sequence
<220> FEATURE:
<223> OTHER INFORMATION: Comparative peptide 4
```

-continued

```
<400> SEQUENCE: 22

Glu Lys Ile Asn Gln Ser Leu Ala Phe Ile Arg Lys Ser Asp Glu Leu
1               5                   10                  15

Leu His Asn Val
            20

<210> SEQ ID NO 23
<211> LENGTH: 20
<212> TYPE: PRT
<213> ORGANISM: Artificial sequence
<220> FEATURE:
<223> OTHER INFORMATION: Comparative peptide 4e
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (8)..(8)
<223> OTHER INFORMATION: (R)-2-(7-octenyl)alanine
<220> FEATURE:
<221> NAME/KEY: MISC_FEATURE
<222> LOCATION: (15)..(15)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 23

Glu Lys Ile Asn Gln Ser Leu Xaa Phe Ile Arg Lys Ser Asp Xaa Leu
1               5                   10                  15

Leu His Asn Val
            20

<210> SEQ ID NO 24
<211> LENGTH: 49
<212> TYPE: PRT
<213> ORGANISM: Artificial sequence
<220> FEATURE:
<223> OTHER INFORMATION: HR2- fragment 476-524

<400> SEQUENCE: 24

Asn Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala Phe Ile Arg
            20                  25                  30

Lys Ser Asp Glu Leu Leu His Asn Val Asn Ala Gly Lys Ser Thr Thr
        35                  40                  45

Asn

<210> SEQ ID NO 25
<211> LENGTH: 38
<212> TYPE: PRT
<213> ORGANISM: Artificial sequence
<220> FEATURE:
<223> OTHER INFORMATION: X-ray of fragment 480-516

<400> SEQUENCE: 25

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His Asn Val Asn
        35
```

<210> SEQ ID NO 26
<211> LENGTH: 35
<212> TYPE: PRT
<213> ORGANISM: Artificial sequence
<220> FEATURE:
<223> OTHER INFORMATION: T108 fragment 478-512

<400> SEQUENCE: 26

Tyr Asp Pro Leu Val Phe Pro Ser Asp Glu Phe Asp Ala Ser Ile Ser
1               5                   10                  15

Gln Val Asn Glu Lys Ile Asn Gln Ser Leu Ala Phe Ile Arg Lys Ser
            20                  25                  30

Asp Glu Leu
        35

<210> SEQ ID NO 27
<211> LENGTH: 35
<212> TYPE: PRT
<213> ORGANISM: Artificial sequence
<220> FEATURE:
<223> OTHER INFORMATION: T118 fragment 488-522

<400> SEQUENCE: 27

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 28
<211> LENGTH: 35
<212> TYPE: PRT
<213> ORGANISM: Artificial Sequence
<220> FEATURE:
<223> OTHER INFORMATION: SAFH-RSVFBD
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (3)..(3)
<223> OTHER INFORMATION: (R)-2-(7-octenyl)alanine
<220> FEATURE:
<221> NAME/KEY: MISC_FEATURE
<222> LOCATION: (10)..(10)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: (R)-2-(7-octenyl)alanine
<220> FEATURE:
<221> NAME/KEY: MISC_FEATURE
<222> LOCATION: (27)..(27)
<223> OTHER INFORMATION: (S)-2-(4-pentenyl)alanine
<220> FEATURE:
<221> NAME/KEY: MISC_FEATURE
<222> LOCATION: (35)..(35)
<223> OTHER INFORMATION: C-term amidated

<400> SEQUENCE: 28

Phe Asp Xaa Ser Ile Ser Gln Val Asn Xaa Lys Ile Asn Gln Ser Leu
1               5                   10                  15

Ala Phe Ile Xaa Lys Ser Asp Glu Leu Leu Xaa Asn Val Asn Ala Gly
            20                  25                  30

Lys Ser Thr
        35

<210> SEQ ID NO 29
<211> LENGTH: 19
<212> TYPE: PRT
<213> ORGANISM: Artificial sequence
<220> FEATURE:
<223> OTHER INFORMATION: comparative peptide 1eg
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (9)..(9)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: (S)-2-(4-pentenyl)alanine
<220> FEATURE:
<221> NAME/KEY: MISC_FEATURE
<222> LOCATION: (19)..(19)
<223> OTHER INFORMATION: C-term amidated

<400> SEQUENCE: 29

Glu Phe Pro Ser Xaa Glu Phe Asp Xaa Ser Ile Xaa Gln Val Asn Xaa
1               5                   10                  15

Lys Ile Asn

<210> SEQ ID NO 30
<211> LENGTH: 20
<212> TYPE: PRT
<213> ORGANISM: Artificial sequence
<220> FEATURE:
<223> OTHER INFORMATION: comparative peptide 4ef
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (1)..(1)
<223> OTHER INFORMATION: (R)-2-(7-octenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (R)-2-(7-octenyl)alanine
<220> FEATURE:
<221> NAME/KEY: MISC_FEATURE
<222> LOCATION: (19)..(19)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 30

Xaa Lys Ile Asn Gln Ser Leu Xaa Phe Ile Arg Xaa Ser Asp Glu Leu
1               5                   10                  15

Leu His Xaa Val
        20

<210> SEQ ID NO 31
<211> LENGTH: 17
<212> TYPE: PRT
<213> ORGANISM: Artificial sequence
<220> FEATURE:
<223> OTHER INFORMATION: comparative peptide 3

<400> SEQUENCE: 31

Glu Gln Ser Leu Ala Phe Ile Arg Lys Ser Asp Glu Leu Leu His Asn
1               5                   10                  15

Val

<210> SEQ ID NO 32
<211> LENGTH: 17
<212> TYPE: PRT
<213> ORGANISM: Artificial sequence
<220> FEATURE:
<223> OTHER INFORMATION: comparative peptide 3a
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (9)..(9)
<223> OTHER INFORMATION: (S)-2-(4-pentenyl)alanine
<220> FEATURE:
<221> NAME/KEY: MISC_FEATURE
<222> LOCATION: (17)..(17)
<223> OTHER INFORMATION: C-term amidated

<400> SEQUENCE: 32

Glu Gln Ser Leu Xaa Phe Ile Arg Xaa Ser Asp Glu Leu Leu His Asn
1               5                   10                  15

Val

<210> SEQ ID NO 33
<211> LENGTH: 20
<212> TYPE: PRT
<213> ORGANISM: Artificial sequence
<220> FEATURE:
<223> OTHER INFORMATION: Consensus for 4a
<220> FEATURE:
<221> NAME/KEY: MISC_FEATURE
<222> LOCATION: (1)..(1)
<223> OTHER INFORMATION: Any amino acid
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: apolar amino acid
<220> FEATURE:
<221> NAME/KEY: MISC_FEATURE
<222> LOCATION: (3)..(3)
<223> OTHER INFORMATION: apolar amino acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)

```
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: apolar amino acid
<220> FEATURE:
<221> NAME/KEY: MISC_FEATURE
<222> LOCATION: (8)..(8)
<223> OTHER INFORMATION: cross-linked amino acid
<220> FEATURE:
<221> NAME/KEY: MISC_FEATURE
<222> LOCATION: (9)..(9)
<223> OTHER INFORMATION: apolar amino acid
<220> FEATURE:
<221> NAME/KEY: MISC_FEATURE
<222> LOCATION: (10)..(10)
<223> OTHER INFORMATION: apolar amino acid
<220> FEATURE:
<221> NAME/KEY: MISC_FEATURE
<222> LOCATION: (11)..(11)
<223> OTHER INFORMATION: polar amino acid
<220> FEATURE:
<221> NAME/KEY: MISC_FEATURE
<222> LOCATION: (12)..(12)
<223> OTHER INFORMATION: cross-linked amino acid
<220> FEATURE:
<221> NAME/KEY: MISC_FEATURE
<222> LOCATION: (13)..(13)
<223> OTHER INFORMATION: Serine
<220> FEATURE:
<221> NAME/KEY: MISC_FEATURE
<222> LOCATION: (14)..(14)
<223> OTHER INFORMATION: Any amino acid
<220> FEATURE:
<221> NAME/KEY: MISC_FEATURE
<222> LOCATION: (15)..(15)
<223> OTHER INFORMATION: Cross-linked amino acid
<220> FEATURE:
<221> NAME/KEY: MISC_FEATURE
<222> LOCATION: (16)..(16)
<223> OTHER INFORMATION: apolar amino acid
<220> FEATURE:
<221> NAME/KEY: MISC_FEATURE
<222> LOCATION: (17)..(17)
<223> OTHER INFORMATION: apolar amino acid
<220> FEATURE:
<221> NAME/KEY: MISC_FEATURE
<222> LOCATION: (18)..(18)
<223> OTHER INFORMATION: Any amino acid
<220> FEATURE:
<221> NAME/KEY: MISC_FEATURE
<222> LOCATION: (19)..(19)
<223> OTHER INFORMATION: Cross-linked amino acid
<220> FEATURE:
<221> NAME/KEY: MISC_FEATURE
<222> LOCATION: (20)..(20)
<223> OTHER INFORMATION: apolar amino acid

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 34
<211> LENGTH: 20
<212> TYPE: PRT
<213> ORGANISM: Artificial sequence
<220> FEATURE:
<223> OTHER INFORMATION: 4a spe
<220> FEATURE:
<221> NAME/KEY: MISC_FEATURE
```

```
<222> LOCATION: (8)..(8)
<223> OTHER INFORMATION: cross-linked amino-acid
<220> FEATURE:
<221> NAME/KEY: MISC_FEATURE
<222> LOCATION: (12)..(12)
<223> OTHER INFORMATION: cross-linked amino-acid
<220> FEATURE:
<221> NAME/KEY: MISC_FEATURE
<222> LOCATION: (15)..(15)
<223> OTHER INFORMATION: cross-linked amino-acid
<220> FEATURE:
<221> NAME/KEY: MISC_FEATURE
<222> LOCATION: (19)..(19)
<223> OTHER INFORMATION: cross-linked amino-acid

<400> SEQUENCE: 34

Glu Lys Ile Asn Gln Ser Leu Xaa Phe Ile Arg Xaa Ser Asp Xaa Leu
1               5                   10                  15

Leu His Xaa Val
            20

<210> SEQ ID NO 35
<211> LENGTH: 20
<212> TYPE: PRT
<213> ORGANISM: Artificial sequence
<220> FEATURE:
<223> OTHER INFORMATION: 4bb-4bb'
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (4)..(4)
<223> OTHER INFORMATION: (S)-2-(4-pentenyl)alanine or (S)-2-
      (4-pentenyl)glycine
<220> FEATURE:
<221> NAME/KEY: MISC_FEATURE
<222> LOCATION: (8)..(8)
<223> OTHER INFORMATION: (S)-2-(4-pentenyl)alanine or (S)-2-
      (4-pentenyl)glycine
<220> FEATURE:
<221> NAME/KEY: MISC_FEATURE
<222> LOCATION: (11)..(11)
<223> OTHER INFORMATION: (S)-2-(4-pentenyl)alanine or (S)-2-
      (4-pentenyl)glycine
<220> FEATURE:
<221> NAME/KEY: MISC_FEATURE
<222> LOCATION: (15)..(15)
<223> OTHER INFORMATION: (S)-2-(4-pentenyl)alanine or (S)-2-
      (4-pentenyl)glycine
<220> FEATURE:
<221> NAME/KEY: MISC_FEATURE
<222> LOCATION: (20)..(20)
<223> OTHER INFORMATION: C-term amidated

<400> SEQUENCE: 35

Glu Lys Ile Xaa Gln Ser Leu Xaa Phe Ile Xaa Lys Ser Asp Xaa Leu
1               5                   10                  15

Leu His Asn Val
            20

<210> SEQ ID NO 36
<211> LENGTH: 20
<212> TYPE: PRT
<213> ORGANISM: Artificial Sequence
<220> FEATURE:
<223> OTHER INFORMATION: 4ca
<220> FEATURE:
<221> NAME/KEY: MISC_FEATURE
<222> LOCATION: (1)..(1)
<223> OTHER INFORMATION: N-term acetylated
<220> FEATURE:
```

```
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 36

Glu Xaa Ile Asn Xaa Ser Leu Xaa Phe Ile Arg Xaa Ser Asp Glu Leu
1               5                   10                  15

Leu His Asn Val
            20

<210> SEQ ID NO 37
<211> LENGTH: 20
<212> TYPE: PRT
<213> ORGANISM: Artificial sequence
<220> FEATURE:
<223> OTHER INFORMATION: V4ca5l1
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 37

Glu Xaa Ile Asn Xaa Ser Leu Xaa Phe Ile Arg Xaa Ser Asp Ala Leu
1               5                   10                  15

Leu His Asn Val
            20

<210> SEQ ID NO 38
<211> LENGTH: 18
<212> TYPE: PRT
<213> ORGANISM: Artificial Sequence
<220> FEATURE:
<223> OTHER INFORMATION: 4ca18
<220> FEATURE:
<221> NAME/KEY: MISC_FEATURE
<222> LOCATION: (1)..(1)
<223> OTHER INFORMATION: N-term acetylated
```

```
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (18)..(18)
<223> OTHER INFORMATION: C-term amidated

<400> SEQUENCE: 38

Glu Xaa Ile Asn Xaa Ser Leu Xaa Phe Ile Arg Xaa Ser Asp Glu Leu
 1               5                  10                  15

Leu His

<210> SEQ ID NO 39
<211> LENGTH: 16
<212> TYPE: PRT
<213> ORGANISM: Artificial Sequence
<220> FEATURE:
<223> OTHER INFORMATION: 4ca16
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (1)..(1)
<223> OTHER INFORMATION: (R)-2-(4-pentenyl)alanine
<220> FEATURE:
<221> NAME/KEY: MISC_FEATURE
<222> LOCATION: (4)..(4)
<223> OTHER INFORMATION: (S)-2-(4-pentenyl)alanine
<220> FEATURE:
<221> NAME/KEY: MISC_FEATURE
<222> LOCATION: (7)..(7)
<223> OTHER INFORMATION: (S)-2-(4-pentenyl)alanine
<220> FEATURE:
<221> NAME/KEY: MISC_FEATURE
<222> LOCATION: (11)..(11)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: C-term amidated

<400> SEQUENCE: 39

Xaa Ile Asn Xaa Ser Leu Xaa Phe Ile Arg Xaa Ser Asp Glu Leu Leu
 1               5                  10                  15

<210> SEQ ID NO 40
<211> LENGTH: 20
<212> TYPE: PRT
<213> ORGANISM: Artificial Sequence
<220> FEATURE:
<223> OTHER INFORMATION: 4ca-var1
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
```

```
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (7)..(7)
<223> OTHER INFORMATION: tBa
<220> FEATURE:
<221> NAME/KEY: MISC_FEATURE
<222> LOCATION: (7)..(7)
<223> OTHER INFORMATION: L-3-tButyl-Alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 40

Glu Xaa Ile Asn Xaa Ser Xaa Xaa Phe Ile Arg Xaa Ser Asp Glu Leu
1               5                   10                  15

Leu His Asn Val
            20

<210> SEQ ID NO 41
<211> LENGTH: 20
<212> TYPE: PRT
<213> ORGANISM: Artificial Sequence
<220> FEATURE:
<223> OTHER INFORMATION: 4ca-var2
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (7)..(7)
<223> OTHER INFORMATION: L-2-Cyclopentyl-Glycine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 41

Glu Xaa Ile Asn Xaa Ser Xaa Xaa Phe Ile Arg Xaa Ser Asp Glu Leu
1               5                   10                  15

Leu His Asn Val
            20
```

```
<210> SEQ ID NO 42
<211> LENGTH: 20
<212> TYPE: PRT
<213> ORGANISM: Artificial Sequence
<220> FEATURE:
<223> OTHER INFORMATION: 4ca-var3
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (7)..(7)
<223> OTHER INFORMATION: 2-Cyclohexyl-L-Glycine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (20)..(20)
<223> OTHER INFORMATION: C-term amidated

<400> SEQUENCE: 42

Glu Xaa Ile Asn Xaa Ser Xaa Xaa Phe Ile Arg Xaa Ser Asp Glu Leu
1               5                   10                  15

Leu His Asn Val
            20

<210> SEQ ID NO 43
<211> LENGTH: 20
<212> TYPE: PRT
<213> ORGANISM: Artificial Sequence
<220> FEATURE:
<223> OTHER INFORMATION: 4ca-var4
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: L-3-tButyl-Alanine
<220> FEATURE:
<221> NAME/KEY: MISC_FEATURE
<222> LOCATION: (20)..(20)
<223> OTHER INFORMATION: C-term amidated
```

```
<400> SEQUENCE: 43

Glu Xaa Ile Asn Xaa Ser Leu Xaa Phe Ile Arg Xaa Ser Asp Glu Xaa
1               5                   10                  15

Leu His Asn Val
            20

<210> SEQ ID NO 44
<211> LENGTH: 20
<212> TYPE: PRT
<213> ORGANISM: Artificial Sequence
<220> FEATURE:
<223> OTHER INFORMATION: 4ca-var5
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: L-3-tButyl-Alanine
<220> FEATURE:
<221> NAME/KEY: MISC_FEATURE
<222> LOCATION: (20)..(20)
<223> OTHER INFORMATION: C-term amidated

<400> SEQUENCE: 44

Glu Xaa Ile Lys Xaa Ser Leu Xaa Phe Ile Arg Xaa Ser Asp Glu Xaa
1               5                   10                  15

Leu His Asn Val
            20

<210> SEQ ID NO 45
<211> LENGTH: 20
<212> TYPE: PRT
<213> ORGANISM: Artificial Sequence
<220> FEATURE:
<223> OTHER INFORMATION: 4ca-var6
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
```

```
<220> FEATURE:
<221> NAME/KEY: MISC_FEATURE
<222> LOCATION: (16)..(16)
<223> OTHER INFORMATION: L-3-tButyl-Alanine
<220> FEATURE:
<221> NAME/KEY: MISC_FEATURE
<222> LOCATION: (20)..(20)
<223> OTHER INFORMATION: C-term amidated

<400> SEQUENCE: 45

Glu Xaa Ile Arg Xaa Ser Leu Xaa Phe Ile Arg Xaa Ser Asp Glu Xaa
1               5                   10                  15

Leu His Asn Val
            20

<210> SEQ ID NO 46
<211> LENGTH: 20
<212> TYPE: PRT
<213> ORGANISM: Artificial Sequence
<220> FEATURE:
<223> OTHER INFORMATION: 4ca-var7
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: 3-Cyclohexyl-L-Alanine
<220> FEATURE:
<221> NAME/KEY: MISC_FEATURE
<222> LOCATION: (20)..(20)
<223> OTHER INFORMATION: C-term amidated

<400> SEQUENCE: 46

Glu Xaa Ile Asn Xaa Ser Leu Xaa Phe Ile Arg Xaa Ser Asp Glu Xaa
1               5                   10                  15

Leu His Asn Val
            20

<210> SEQ ID NO 47
<211> LENGTH: 18
<212> TYPE: PRT
<213> ORGANISM: Artificial Sequence
<220> FEATURE:
<223> OTHER INFORMATION: 4ca-var8
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
```

```
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: L-3-tButyl-Alanine
<220> FEATURE:
<221> NAME/KEY: MISC_FEATURE
<222> LOCATION: (18)..(18)
<223> OTHER INFORMATION: C-term amidated

<400> SEQUENCE: 47

Glu Xaa Ile Asn Xaa Ser Leu Xaa Phe Ile Arg Xaa Ser Asp Glu Xaa
1               5                   10                  15

Leu His

<210> SEQ ID NO 48
<211> LENGTH: 20
<212> TYPE: PRT
<213> ORGANISM: Artificial Sequence
<220> FEATURE:
<223> OTHER INFORMATION: 4ca-var9
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)alanine
<220> FEATURE:
<221> NAME/KEY: MISC_FEATURE
<222> LOCATION: (8)..(8)
<223> OTHER INFORMATION: (S)-2-(4-pentenyl)alanine
<220> FEATURE:
<221> NAME/KEY: MISC_FEATURE
<222> LOCATION: (12)..(12)
<223> OTHER INFORMATION: (S)-2-(4-pentenyl)alanine
<220> FEATURE:
<221> NAME/KEY: MISC_FEATURE
<222> LOCATION: (16)..(16)
<223> OTHER INFORMATION: L-3-tButyl-Alanine
<220> FEATURE:
<221> NAME/KEY: MISC_FEATURE
<222> LOCATION: (17)..(17)
<223> OTHER INFORMATION: L-3-tButyl-Alanine
<220> FEATURE:
<221> NAME/KEY: MISC_FEATURE
<222> LOCATION: (20)..(20)
<223> OTHER INFORMATION: C-term amidated

<400> SEQUENCE: 48

Glu Xaa Ile Asn Xaa Ser Leu Xaa Phe Ile Arg Xaa Ser Asp Glu Xaa
1               5                   10                  15

Xaa His Asn Val
            20

<210> SEQ ID NO 49
<211> LENGTH: 20
<212> TYPE: PRT
<213> ORGANISM: Artificial Sequence
<220> FEATURE:
```

```
<223> OTHER INFORMATION: 4ca2
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (2)..(2)
<223> OTHER INFORMATION: (R)-2-(4-pentenyl)alanine
<220> FEATURE:
<221> NAME/KEY: MISC_FEATURE
<222> LOCATION: (5)..(5)
<223> OTHER INFORMATION: (S)-2-(4-pentenyl)glycine
<220> FEATURE:
<221> NAME/KEY: MISC_FEATURE
<222> LOCATION: (8)..(8)
<223> OTHER INFORMATION: (S)-2-(4-pentenyl)glycine
<220> FEATURE:
<221> NAME/KEY: MISC_FEATURE
<222> LOCATION: (12)..(12)
<223> OTHER INFORMATION: (S)-2-(4-pentenyl)glycine
<220> FEATURE:
<221> NAME/KEY: MISC_FEATURE
<222> LOCATION: (20)..(20)
<223> OTHER INFORMATION: C-term amidated

<400> SEQUENCE: 49

Glu Xaa Ile Asn Xaa Ser Leu Xaa Phe Ile Arg Xaa Ser Asp Glu Leu
1               5                   10                  15

Leu His Asn Val
            20

<210> SEQ ID NO 50
<211> LENGTH: 20
<212> TYPE: PRT
<213> ORGANISM: Artificial Sequence
<220> FEATURE:
<223> OTHER INFORMATION: 4a2
<220> FEATURE:
<221> NAME/KEY: MISC_FEATURE
<222> LOCATION: (1)..(1)
<223> OTHER INFORMATION: N-term acetylated
<220> FEATURE:
<221> NAME/KEY: MISC_FEATURE
<222> LOCATION: (8)..(8)
<223> OTHER INFORMATION: (S)-2-(4-pentenyl)glycine
<220> FEATURE:
<221> NAME/KEY: MISC_FEATURE
<222> LOCATION: (12)..(12)
<223> OTHER INFORMATION: (S)-2-(4-pentenyl)glycine
<220> FEATURE:
<221> NAME/KEY: MISC_FEATURE
<222> LOCATION: (15)..(15)
<223> OTHER INFORMATION: (S)-2-(4-pentenyl)glycine
<220> FEATURE:
<221> NAME/KEY: MISC_FEATURE
<222> LOCATION: (19)..(19)
<223> OTHER INFORMATION: (S)-2-(4-pentenyl)glycine
<220> FEATURE:
<221> NAME/KEY: MISC_FEATURE
<222> LOCATION: (20)..(20)
<223> OTHER INFORMATION: C-term amidated

<400> SEQUENCE: 50

Glu Lys Ile Asn Gln Ser Leu Xaa Phe Ile Arg Xaa Ser Asp Xaa Leu
1               5                   10                  15

Leu His Xaa Val
            20
```

FUSION RESPIRATORY SYNCYTIAL VIRUS INHIBITORS AND USE THEREOF

CROSS-REFERENCE TO RELATED APPLICATION

This application is the U.S. national stage application of International Patent Application No. PCT/EP2017/054966, filed Mar. 2, 2017.

The Sequence Listing for this application is labeled "Seq-List.txt" which was created on Jul. 26, 2018 and is 40 KB. The entire content of the sequence listing is incorporated herein by reference in its entirety.

FIELD OF THE INVENTION

The present invention relates to inhibitors of human respiratory syncytial virus and their use in the prevention and/or treatment of RSV derived disorders, in particular lower respiratory infections.

BACKGROUND OF THE INVENTION

Lower respiratory infection is one of the leading causes of human death worldwide, and is the most important cause of mortality in infants. Among the pathogens responsible for these infections, human respiratory syncytial virus (RSV) accounts for approximately 20% of all lower respiratory infections in infants (Hall et al., 2009, *N. Engl. J. Med.*, 360:588-598). The global incidence of infant mortality due to RSV is the highest in developing countries, and though it is much lower in developed countries, it is a high burden on the health care systems because of the large number of children that must be hospitalized. In 2005, RSV caused almost 34 million cases of lower respiratory infections in children under 5 years of age, 3-10% of them requiring hospitalization, accounting for 45% of the total child admissions.

RSV can also cause fatal respiratory tract infections in fragile or immune-compromised individuals. RSV is estimated to cause on average 17,358 deaths annually in the United States, with 78% of these deaths occurring in adults over age 65 and is suspected to be the main cause for recurrent asthma in children. Recently, RSV has been recognized as a significant cause of severe respiratory infections in the elderly. In a study performed in the USA, the mortality rates were found to be higher in the elderly than in the children (Thompson et al., 2003, United States. JAMA, 289:179-186).

Respiratory Syncytial Virus (RSV) infects calves under the age of two. These viruses are responsible for more than 70% of bronchiolitis in both species.

No vaccine is presently available against RSV, even if many trials have been done, and due to the immunopathological component of the symptoms, immunization with this virus is challenging, especially in the very young population. Treatment options are limited to the prophylactic treatment of at-risk infants with the mAb palivizumab (Synagis) and to controversial therapeutic intervention with the nucleoside analog ribavirin (Rebetol) (Collins et al., 2011, *Virus Res.*, 162:80-99). The clinical use of these agents is limited and there is a need for a more effective treatment for the at-risk population.

The RSV fusion glycoprotein F is the focus of active research in the field of vaccines, antibodies and small-molecules. The antiviral compounds currently investigated in clinical settings are GS-5806 (DeVincenzo et al., 2014, *N. Engl. J. Med.*, 371:711-722), a small molecule fusion inhibitor ($EC_{50}$=0.4 nM) and JNJ-53718678 (Roymans et al., 2015, *Archives de pediatrie*, 22:215), and ALX-0171, a trimeric nanobody that binds the antigenic site II of F with subnanomolar affinity (Detalle et al., 2015, *Antimicrob. Agents Chemother.*, doi:10.1128/AAC.01802-15). RSV F is a type I fusion protein that undergoes a conformation change from a metastable prefusion state to a fully stabled postfusion state upon binding to nucleolin (Tayyari et al., 2011, *Nat. Med.*, 17:1132-1135), thereby enabling the fusion of the viral membrane with the cell membrane. The driving force of this process resides in the folding of two heptad repeat regions from the N-terminal and C-terminal segments of F, named HR1 and HR2, which fold into a six-helix bundle conformation (Zhao et al., 2000, *Proc. Natl. Acad. Sci. USA*, 97:14172-14177; Yin et al., 2006, *Nature*, 439:38-44). Peptides derived from these domains can function as dominant-negative inhibitors by binding to the transiently exposed coiled coil in the prehairpin fusion intermediate. The RSV HR2 region (476-524) is a 49 amino acid sequence that has been extensively characterized (FIG. 1). HR2 is a largely unstructured peptide in aqueous solution folding into an α-helix upon binding to trimeric HR1 coiled coil (Matthews et al., 2000, *J. Virol.*, 74:5911-5920). X-ray structure analysis revealed that only part of HR2 (485-515) folds into an α-helix (Zhao et al., 2000, supra).

Synthetic peptides derived from the RSV HR2 native domain having antiviral properties capable to block virus syncytium formation were identified (Lambert et al., 1996, *Proc. Natl. Acad. Sci. USA*, 93:2186-2191). The authors did not report further progress, probably because of the poor inhibitory potencies of this class of peptides and due to a weaker affinity of the HR2 peptides for the trimeric HR1 fusion intermediate. Alternatively, it has been suggested that the decreased potency may also be due to differences in the fusion kinetics (Porotto et al., 2009, *J. Virol.*, 83:6947-6951) and efforts in bypassing this issue by stabilizing the α-helical nature of the peptide in the unbound state through chemical cross-linking of amino-acid side chains that are not interacting with the target, thereby decreasing the entropic cost for binding to the target have let to RSV HR2 peptides stabilized with cross-lactam bridges (Shepherd et al., 2006, *J. Am. Chem. Soc.*, 128:13284-13289). However, these compounds were not druggable, because of the nature of the cross linking bridges which are susceptible to proteolytic degradation in the serum. Recently, further constrained peptides derived from T118 have been reported, a 35-amino-acid-long HR2 segment (Lambert et al., 1996, supra; Bird et al., 2014, *J. Clin. Invest.*, 124:2113-2124) where non-natural olefinic amino acids are inserted into the peptides, and the olefinic side chains are crosslinked by ruthenium catalyzed metathesis. The RSV F protein from bRSV is 82% identical at the amino acid level to the hRSV F protein, and amino acid residues known to confer drug resistance to fusion inhibitors in hRSV are 100% conserved. The small-molecules fusion inhibitors BMS-433771 (Yu, 2007, *Bioorganic & Medicinal Chemistry Letters*, 17, 895-901), TMC-353121 (Bonfanti et al., 2008, *J Med Chem*, 51:875-896) and GS1, a close structural analog of GS-5806 (Jordan et al., 2015, *Antimicrobial Agents and Chemotherapy*, 59(8), 4889-4900) have been shown to be active against hRSV and bRSV.

Due to the severity of the pathologies or disorders resulting from infections by respiratory syncytial virus (SV), in particular in infants, there is a high need to develop new substances and methods of prevention and/or treatment of RSV derived disorders.

SUMMARY OF THE INVENTION

The present invention is directed to the unexpected finding of novel short double stapled peptides, which display nanomolar potency in HEp-2 cells, and are exceptionally robust to degradation in the presence of proteolytic enzymes. Those peptides are two times shorter than T118, one of the best native peptide reported previously, but are 10-fold more potent inhibitors despite the significant difference in length.

It is an object of the invention to provide new inhibitors of RSV fusion with the host cell membrane with improved stability, in particular in view of the pharmaceutical use and formulation.

A first aspect of the invention provides a compound of SEQ ID NO.: 1, as well as pharmaceutically acceptable salts and pharmaceutically active variants thereof.

Another aspect of the invention relates to a pharmaceutical composition comprising at least one compound according to the invention and at least one pharmaceutically acceptable carrier.

Another aspect of the invention resides in a compound according to the invention for use in the prevention and/or treatment of RSV infections, in particular human or bovine RSV, and any related disorders thereof including lower respiratory infections.

Another aspect of the invention resides in a use of a compound according to the invention for the preparation of a medicament for the prevention and/or treatment of a RSV infection, in particular human RSV, and any related disorders thereof including lower respiratory infection.

Another aspect of the invention is a method for preventing and/or treating a subject suffering from a RSV infection, in particular human RSV infection, and any related disorders thereof including lower respiratory infections, comprising administering a compound according to the invention or a pharmaceutical formulation thereof in a subject in need thereof.

Further objects and advantageous aspects of the invention will be apparent from the claims and/or from the following detailed description of embodiments of the invention with reference to the annexed drawings.

BRIEF DESCRIPTION OF THE DRAWINGS

FIG. 2 compares the different sequences of peptides of the invention with comparative peptides. A: Table 2 represents peptides of the invention and comparative peptides tested in the Examples; B: Table 3 represents further comparative peptides.

FIG. 3 shows the properties of the peptides of the invention as compared to comparative peptides SAH-RSV$_{BD}$ isomers and 4. A: Circular dichroism spectropolarimetry as described in Example 1; B: Peptide effects upon RSV-GFP infection of A549 cells as described in Example 2; C: Chymotrypsin and D: trypsin resistance profiles of peptides. Data (mean±SEM) represent fraction intact for experiments performed in triplicate and in duplicate, respectively.

DETAILED DESCRIPTION OF THE INVENTION

Figure 1:
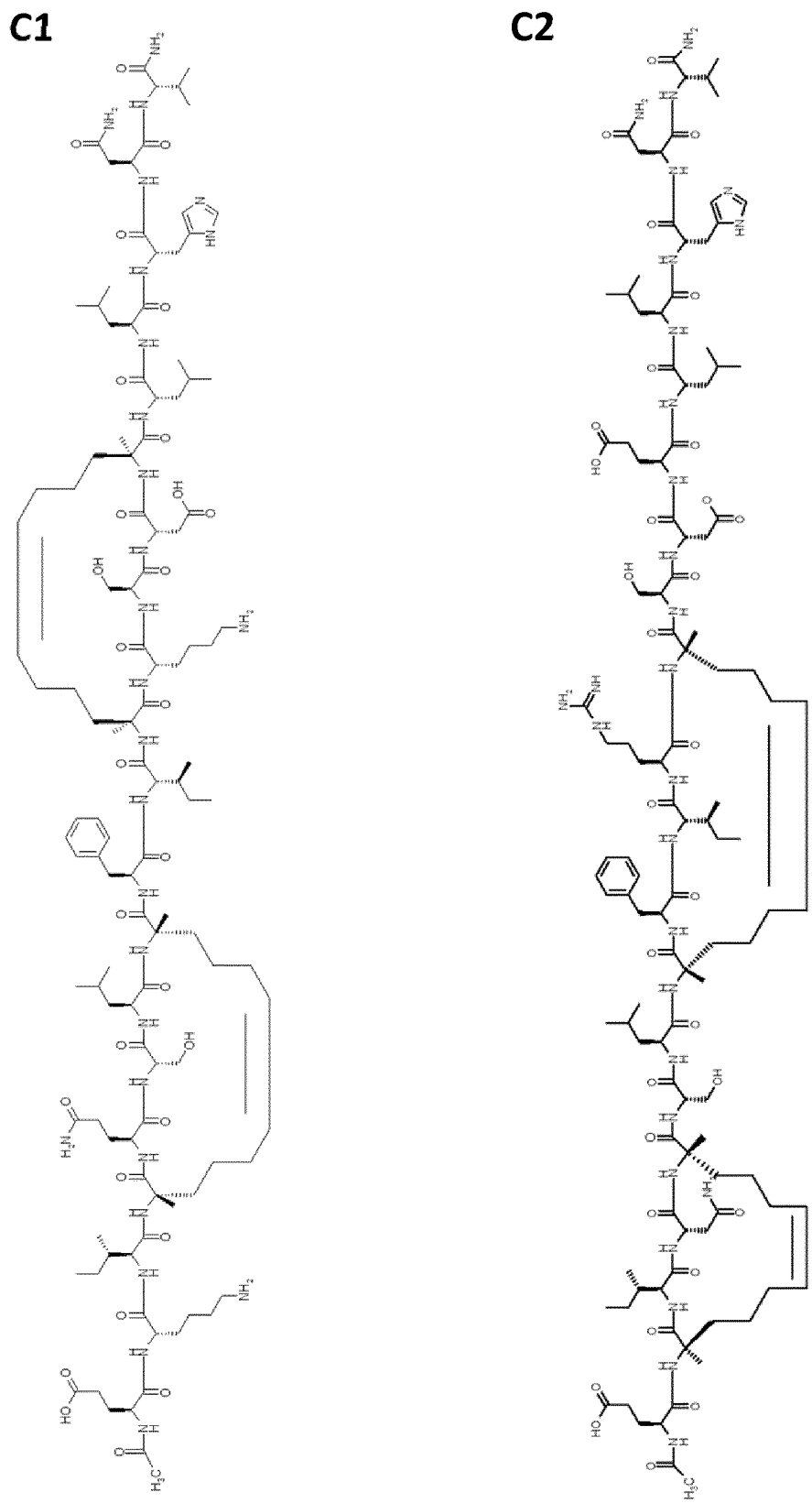
FIG. 1 represents schematically the structure of the RSV fusion glycoprotein F and peptide sequences within the HR-2 domain. A: prior to maturation of RSV fusion glycoprotein F, the F1 domain is linked to the F2 domain via a disulfide bridge. FP: fusion peptide, HR1: heptad repeat 1, HR2: heptad repeat 2, TM: transmembrane domain; B: sequences of the full-length of the HR-2 domain (SEQ ID NO.: 24) where the arrow indicates the region (SEQ ID NO.: 25) observed as an α-helix in the x-ray structure of the post-fusion structure (the PDB accession number is 1G2C), of reference peptides T108 and T1118 (SEQ ID NO.: 26 and SEQ ID NO.: 27) and double stapled peptides of the invention 4bb, 4ca, 4a, 3ac, (SEQ ID NO.: 2, 3, 19 and 20 respectively) and comparative peptide SAH-RSV$_{BD}$ (SEQ ID NO.: 28), 8=(R)-2-(7-octenyl)alanine, X=(S)-2-(4-pentenyl)alanine and "+"=(R)-2-(4-pentenyl)alanine; C: represents the chemical structures of peptides of the invention 4bb (C1), 4ca (C2), 4bb' (C3), 4a (C4) 3ac (C5), 4ca2 (C6) and 4a2 (C7).
Figure 1:
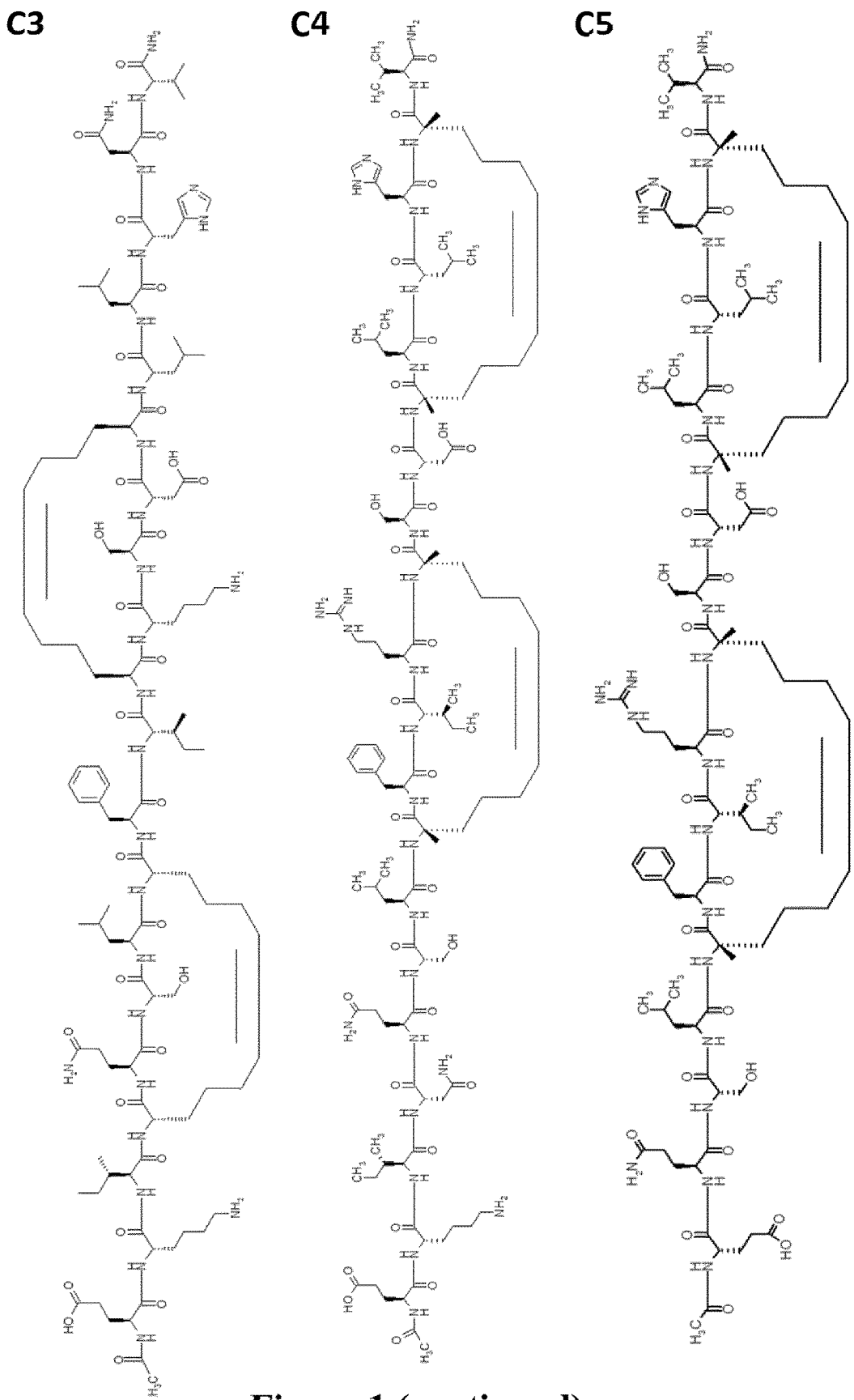

The term "efficacy" of a treatment according to the invention can be measured based on changes in the course of disease in response to a use according to the invention. For example, the efficacy of a treatment according to the invention can be measured by a decrease. As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease.

The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions. For example, the ability of the compounds of invention in inhibiting RSV fusion can be tested in known assays such as an antiviral MTT assay, a virus yield reduction assay, effect of time addition, virus inactivation, inhibition on viral RNA and protein synthesis, resistance studies (Andries, 2003, *Antiviral Res.*, 60 209-219), plaque assay, syncytia formation assay, viral fusion assay, genotypic profiling or those described therein.

As another example, the efficacy of the compounds of invention in the treatment of RSV related disorders can be assayed in the viral load, total mucus weight, sputum, change from baseline in total symptom-diary scores to the end of the quarantine period. The term "subject" as used herein refers to mammals. For examples, mammals contemplated by the present invention include human, primates, domesticated animals such as cattle, sheep, pigs, horses, laboratory rodents and the like.

The term "pharmaceutically active derivative" refers to any compound that upon administration to the recipient, is capable of providing directly or indirectly, the activity disclosed herein.

The term "cross-linking bridge" or "staple" refers to cross-linking between two non-contiguous amino acid residues of a peptide obtained via a hydrocarbon "staple" selected from an olefin-containing side chain such as described in Kim et al., 2011, *Nature Protocols* 6, 761-771; Verdine et al., 2011, *Methods in Enzymology*, 503, 3-33, and obtainable by ring-closing olefin metathesis (RCM), a disulfide bridge such as described in Jackson et al., 1991, *Journal of the American Chemical Society*, 113(24) 9391-9392; an ABA (4-aminobenzoic acid) residue, AMBA (4-(aminomethyl, benzoic acid) residue, APA (4-aminophenyl acetic acid) residue and AMPA (p-(aminomethyl)phenylacetic acid) residue with ((S)-2,3-diaminopropionic acid residue (Dap) in position 3 is linked to Glu¹⁰ via the carboxyl function of a bridging 4-(aminomethyl)phenylacetic acid residue) staple such as described in Yu et al., 1999, *Bioorganic and Medicinal Chemistry*, 7(1), 161-175; a lactam-bridge such as described in Ösapay et al., 1992, *Journal of the American Chemical Society*, 114 (18), 6966-6973, 1992, a disulfide bridge (Jackson et al., 1991, *Journal of the American Chemical Society*, 113(24) 9391-9392, a thio-based bridge (Mas-Moruno, *Angew. Chem. Int. ed.* 2011, 50, 9496), a thioether bond, biaryl-bridges, bridges obtained through the incorporation of heterocycles, and carbon-carbon bonds (White et al., 2011, *Nat. Chem.*, 3, 509; Marsault et al., 2011, *J. Med. Chem.*, 54, 1961) and perfluoroaromatic staples (Spokoyny et al., 2013, *Journal of the American Chemical Society*, 135, 5946-5949). Alternatively, the crosslinking bridges between the aminoacids are achieved via double olefin bearing amino acids which allow forming dual hydrocarbon staples emerge from common attachment points in the peptide as described in Hilinski et al., 2014, *JACS*, 136, 12314-12322. In this case, only three olefin-bearing amino acids are necessary to form a total of two cross-linking bridges.

According to a particular embodiment, cross-linked amino acids are of the following Formula (III):

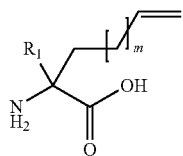

(III)

wherein $R^1$ is a residue from a natural or non-natural such as alanine or glycine (e.g. methyl or H) and m is an integer from 0 to 5, such as from 2 to 5, in particular 2. According to a particular embodiment, cross-linked amino acids are selected from —(S)-2-(3-butenyl)alanine, —(R)-2-(3-butenyl)alanine, (S)-2-(4-pentenyl)alanine, (R)-2-(4-pentenyl)alanine, —(S)-2-(5-hexenyl)alanine, (R)-2-(5-hexenyl)alanine —(S)-2-(6-heptenyl)alanine, —(R)-2-(6-heptenyl)alanine, (S)-2-(7-octenyl)alanine, (R)-2-(7-octenyl)alanine, —(S)-2-(3-butenyl)glycine, —(R)-2-(3-butenyl)glycine (S)-2-(4-pentenyl)glycine, (R)-2-(pentenyl)glycine, —(S)-2-(5-hexenyl)glycine, (R)-2-(5-hexenyl)glycine —(S)-2-(6-heptenyl)glycine, —(R)-2-(6-heptenyl)glycine (S)-2-(7-octenyl)glycine and (R)-2-(7-octenyl)glycine and 2,2-bis(4-pentenyl)glycine.

According to a further particular embodiment, cross-linked amino acids are selected from (S)-2-(4-pentenyl)alanine, (R)-2-(4-pentenyl)alanine and (R)-2-(4-pentenyl)glycine.

According to a further particular embodiment, cross-linked amino acids are (S)-2-(4-pentenyl)glycine.

According to a further particular embodiment, cross-linked amino acids are selected from (S)-2-(4-pentenyl)alanine.

According to a further particular embodiment, cross-linked amino acids are selected from (S)-2-(4-pentenyl)alanine and (R)-2-(4-pentenyl)alanine.

According to a further particular embodiment, cross-linked amino acids are selected from (R)-2-(4-pentenyl)alanine and (S)-2-(4-pentenyl)glycine.

According to a particular embodiment, cross-linked amino acids are of Formula (III) wherein $R^1$ is methyl and m is an integer from 2 to 5, in particular 2.

According to a particular embodiment, cross-linked amino acids are of the following Formula (IV):

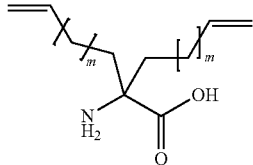

(IV)

wherein and m is an integer from 0 to 5, such as from 2 to 5, in particular 2.

According to another particular embodiment, cross-linked amino acids are of Formula (IV) wherein m is an integer from 2 to 5, in particular 2.

According to a particular embodiment, cross-linked amino acids are selected from one olefin bearing aminoacids such as on (S)-α-methyl,α-pentenylglycine and (S)-α-methyl,α-octenylglycine or (R)-α-methyl, α-pentenylglycine and (R)-α-methyl,α-octenylglycine and two olefin-bearing amino acids such as bispentenylglycine (B5, 2-(((9H-Fluoren-9-yl)methoxy)-carbonylamino)-2-(pent-4-enyl)hept-6-enoic acid).

The term "variant", applied to a peptide or polypeptide, as referred to herein means a peptide or polypeptide substantially homologous to the referenced peptide sequence, but which has at least one amino acid different from that of the referenced sequence because of one or more amino acid deletion, insertion and/or substitution. Substantially homologous means a variant amino acid sequence which is identical to the referenced peptide sequence except for the deletion, insertion and/or substitution of 1, 2, 3, 4, 5 or 6 amino acid residues. In a more particular embodiment, a variant amino acid sequence is identical to the referenced peptide sequence except for the deletion and/or conservative substitution of 1, 2, 3, 4, 5 or 6 amino acid residues. The identity of two amino acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physicochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Amino acid hydrophobicity can be found on the basis of known scales such as Kyte, et al, 1982, *J. Mol. Biol.*, 157: 105-131; Eisenberg, 1984, *Ann. Rev. Biochem.*, 53: 595-623. Other such conservative substitutions, for example, substitutions of entire regions having similar hydrophobicity characteristics or α-helical propensity, are well known (Kyte, et al, 1982, supra). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Tables 1a and 1b below. The term "variant" also includes a peptide or polypeptide substantially homologous to the referenced peptide sequence, but which has an amino acid sequence different from that of the referenced sequence because one or more amino acids have been chemically modified or substituted by amino acids analogs. For example non-natural residues can be introduced to enhance the pharmacological properties of peptide-based therapeutics (Geurink et al., 2013, *J. Med. Chem.*, 56, 1262; Rand et al., 2012, Med. *Chem. Commun,* 3, 1282). According to a particular embodiment, apolar amino acid according to the invention can be a non-natural amino acid. In particular, an apolar amino acid can be selected from a non-polar amino acid from Table 1a:

TABLE 1a

| Name | Abbreviation | Structure |
|---|---|---|
| L-2-Cyclopentyl-Glycine | Cpg | 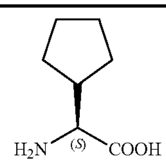 |
| L-3-tButyl-Alanine | tBa | 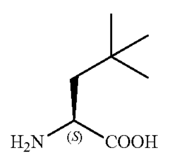 |
| 3-Cyclohexyl-L-Alanine | Cha | 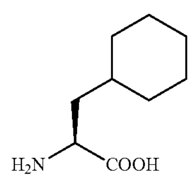 [SMILES: N[C@@H](CC1CCCCC1)C(=O)O] |
| 2-Cyclohexyl-L-Glycine | Chg | 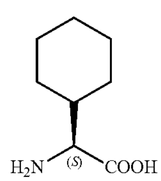 |

The term "indirectly" also encompasses active forms of compounds of the invention into which the compounds of Formula (I) may be converted for example via endogenous enzymes or metabolism. Compounds of Formula (I) comprise chemically or metabolically decomposable groups and may be converted into a pharmaceutically active compound in vivo under physiological conditions.

The invention further encompasses any tautomers, geometrical isomers, optically active forms as enantiomers, diastereomers and racemate forms of the compounds according to the invention.

TABLE 1b

| Amino acids | Examples of « conservative » substitutions |
|---|---|
| Ala (A) | Val, Leu, Ile |
| Arg (R) | Lys, Gln, Asn |
| Asn (N) | Gln |
| Asp (D) | Glu |

TABLE 1b-continued

| Amino acids | Examples of « conservative » substitutions |
|---|---|
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe, Norleucine |
| Leu (L) | Ile, Val, Met, Ala, Phe, Norleucine |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Trp (W) | Phe, Tyr |
| Thr (T) | Ser |
| Tyr (Y) | Trp, Phe, Thr, Ser |
| Val (V) | Ile Met, Leu, Phe, Ala, Norleucine |

According to another particular embodiment, the peptides of the invention can be optionally acetylated at the N-terminus and/or amidated at the C-terminus.

The term "pharmaceutical formulation" refers to preparations which are in such a form as to permit biological activity of the active ingredient(s) to be unequivocally effective and which contain no additional component which would be toxic to subjects to which the said formulation would be administered.

Compounds of the Invention

According to one aspect, is provided a compound comprising the following amino acid sequence:
Xaa1 Xaa2 Xaa3 Xaa4 Xaa5 Xaa6 Xaa7 Xaa8 Xaa9 Xaa10 Xaa11 Xaa12 Xaa13 Xaa14 Xaa15 Xaa16 Xaa17 Xaa18 Xaa19 Xaa20 (SEQ ID NO: 1), wherein Xaa1, Xaa6, Xaa14 and Xaa18 are independently selected from any amino acid; Xaa2, Xaa4, Xaa5 and Xaa19 are independently selected from any amino acid or a cross-linked amino-acid; Xaa3, Xaa7, Xaa9, Xaa10, Xaa16, Xaa17 and Xaa20 are an independently selected apolar amino acid. Examples of apolar amino-acid comprise Ile, Leu, Phe, Val and Ala; Xaa8 is a cross-linked amino-acid; Xaa11 and Xaa12 are independently selected from a polar amino acid and a cross-linked amino-acid. Examples of polar amino-acid comprise Arg, Lys, Asp and Glu; Xaa13 is Serine and Xaa15 is selected from a polar amino acid, such as Glu, Asp, Arg, and Lys and a cross-linked amino-acid, wherein the peptide contains a total of two cross-linking bridges, each between two cross-linked amino acids spaced by 2 or three amino-acids (i, i+3 and/or i, i+4 staples), as well as pharmaceutically acceptable salts and pharmaceutically active variants thereof.

According to a particular embodiment, is provided a compound consisting of SEQ ID NO: 1 and pharmaceutically active variants thereof.

According to another particular aspect, a pharmaceutically active variant according to the invention consists in SEQ ID NO: 1 wherein 1, 2, 3, 4, 5 or 6 amino acid residues have been deleted at positions not bearing a cross-linked bridge.

According to another further particular aspect, a pharmaceutically active variant according to the invention consists in SEQ ID NO: 1 wherein 1 or 2 amino acid residues have been deleted at the N-terminus when those positions not bearing a cross-linked bridge.

According to another further particular aspect, a pharmaceutically active variant according to the invention consists in SEQ ID NO: 1 wherein 1, 2 or 3 amino acid residues have been deleted at the C-terminus when those positions not bearing a cross-linked bridge.

According to a further aspect, is provided a compound comprising the amino acid sequence of SEQ ID NO: 1, wherein Xaa1 is Glu or Ala, more particularly Glu.

According to a further aspect, is provided a compound comprising the amino acid sequence of SEQ ID NO: 1, wherein Xaa2 is Lys or Ala, more particularly Lys or a cross-linked amino-acid, in particular (R)-2-(4-pentenyl)alanine.

According to a further aspect, is provided a compound comprising the amino acid sequence of SEQ ID NO: 1, wherein Xaa3 is Ile or Ala, more particularly Ile.

According to a further aspect, is provided a compound comprising the amino acid sequence of SEQ ID NO: 1, wherein Xaa4 is Asn, Glu or a cross-linked amino-acid, in particular (S)-2-(4-pentenyl)alanine.

According to a further aspect, is provided a compound comprising the amino acid sequence of SEQ ID NO: 1, wherein Xaa5 is Gln or a cross-linked amino-acid, in particular (S)-2-(4-pentenyl)alanine.

According to a further aspect, is provided a compound comprising the amino acid sequence of SEQ ID NO: 1, wherein Xaa6 is Ser or Ala, more particularly Ser.

According to a further aspect, is provided a compound comprising the amino acid sequence of SEQ ID NO: 1, wherein Xaa7 is Leu or Ala, more particularly Leu.

According to a further aspect, is provided a compound comprising the amino acid sequence of SEQ ID NO: 1, wherein Xaa7 is a non-natural apolar amino acid, more particularly one selected from Cpg, tBa, Cha and Chg, in particular Cpg, tBa and Chg.

According to a further aspect, is provided a compound comprising the amino acid sequence of SEQ ID NO: 1, wherein Xaa8 is (S)-2-(4-pentenyl)alanine.

According to a further aspect, is provided a compound comprising the amino acid sequence of SEQ ID NO: 1, wherein Xaa9 is Phe or Ala, more particularly Phe.

According to a further aspect, is provided a compound comprising the amino acid sequence of SEQ ID NO: 1, wherein Xaa10 is Ile or Ala, more particularly Ile. According to a further aspect, is provided a compound comprising the amino acid sequence of SEQ ID NO: 1, wherein Xaa11 is Arg or a cross-linked amino-acid, in particular (S)-2-(4-pentenyl)alanine.

According to a further aspect, is provided a compound comprising the amino acid sequence of SEQ ID NO: 1, wherein Xaa12 is Lys or a cross-linked amino-acid, in particular (S)-2-(4-pentenyl)alanine.

According to a further aspect, is provided a compound comprising the amino acid sequence of SEQ ID NO: 1, wherein Xaa14 is Asp or Ala, more particularly Asp.

According to a further aspect, is provided a compound comprising the amino acid sequence of SEQ ID NO: 2, wherein Xaa15 is Glu or a cross-linked amino-acid, in particular (S)-2-(4-pentenyl)alanine.

According to a further aspect, is provided a compound comprising the amino acid sequence of SEQ ID NO: 1, wherein Xaa16 is Leu or Ala, more particularly Leu.

According to a further aspect, is provided a compound comprising the amino acid sequence of SEQ ID NO: 1, wherein Xaa16 is a non-natural apolar amino acid, more particularly one selected from Cpg, tBa, Cha and Chg, in particular tBa and Cha.

According to a further aspect, is provided a compound comprising the amino acid sequence of SEQ ID NO: 1, wherein Xaa17 is Leu or Ala, more particularly Leu.

According to a further aspect, is provided a compound comprising the amino acid sequence of SEQ ID NO: 1, wherein Xaa17 is a non-natural apolar amino acid, more particularly one selected from Cpg, tBa, Cha and Chg, in particular tBa.

According to a further aspect, is provided a compound comprising the amino acid sequence of SEQ ID NO: 1, wherein Xaa18 is His or Ala, more particularly His.

According to a further aspect, is provided a compound comprising the amino acid sequence of SEQ ID NO: 1, wherein Xaa19 is Asn, Ala, more particularly Asn or a cross-linked amino-acid, in particular (S)-2-(4-pentenyl)alanine.

According to a further aspect, is provided a compound comprising the amino acid sequence of SEQ ID NO: 1, wherein Xaa20 is Val or Ala, more particularly Val.

According to another further embodiment, is provided a peptide of the invention comprising the amino acid sequence of SEQ ID NO: 1, wherein Xaa4, Xaa8, Xaa11 and Xaa15 are each independently a cross-linked amino-acid (SEQ ID NO: 2).

According to another further embodiment, is provided a peptide of the invention comprising the following amino acid sequence: Glu Lys Ile Xaa4 Gln Ser Leu Xaa8 Phe Ile Xaa11 Lys Ser Asp Xaa15 Leu Leu His Asn Val (SEQ ID NO: 3), wherein Xaa4, Xaa8, Xaa11 and Xaa15 are each independently a cross-linked amino-acid, for example independently a cross-linked amino-acid of Formula (III), as well as pharmaceutically acceptable salts and pharmaceutically active variants thereof.

According to another further embodiment, is provided a peptide of the invention comprising a sequence of SEQ ID NO: 2 or 3, wherein the cross-linked amino-acids are (S)-2-(4-pentenyl)alanine.

According to another further embodiment, is provided a peptide of the invention comprising a sequence of SEQ ID NO: 2 or 3, wherein the cross-linked amino-acids are (S)-2-(4-pentenyl)glycine.

According to another further embodiment, is provided a peptide of the invention of SEQ ID NO: 35.

According to another further embodiment, is provided a peptide of the invention of formula (C1).

According to another further embodiment, is provided a peptide of the invention of formula (C3).

According to another further embodiment, is provided a peptide of the invention comprising the amino acid sequence of SEQ ID NO: 1, wherein Xaa2, Xaa5, Xaa8 and Xaa12 are each independently a cross-linked amino-acid are each independently a cross-linked amino-acid (SEQ ID NO: 17).

According to another further embodiment, is provided a peptide of the invention comprising the following amino acid sequence: Glu Xaa2 Ile Asn Xaa5 Ser Leu Xaa8 Phe Ile Arg Xaa12 Ser Asp Glu Leu Leu His Asn Val (SEQ ID NO: 18), wherein Xaa2, Xaa5, Xaa8 and Xaa12 are each independently a cross-linked amino-acid, as well as pharmaceutically acceptable salts and pharmaceutically active variants thereof.

According to another further embodiment, is provided a peptide of the invention comprising a sequence of SEQ ID NO: 17 or 18, wherein the cross-linked amino-acids are (S)-2-(4-pentenyl)alanine or (R)-2-(4-pentenyl)alanine.

According to another further embodiment, is provided a peptide of the invention comprising a sequence of SEQ ID NO: 17 or 18, wherein the cross-linked amino-acids are (R)-2-(4-pentenyl)alanine or (S)-2-(4-pentenyl)glycine.

According to another further embodiment, is provided a peptide of the invention comprising a sequence of SEQ ID NO: 17 or 18, wherein the cross-linked amino-acids Xaa5, Xaa8 and Xaa12 are (S)-2-(4-pentenyl) alanine and Xaa2 is (R)-2-(4-pentenyl)alanine.

According to another further embodiment, is provided a peptide of the invention comprising a sequence of SEQ ID NO: 17 or 18, wherein the cross-linked amino-acids Xaa5, Xaa8 and Xaa12 are (S)-2-(4-pentenyl)glycine and Xaa2 is (R)-2-(4-pentenyl)alanine.

According to another further embodiment, is provided a peptide of the invention of SEQ ID NO: 36.

According to another further embodiment, is provided a peptide of the invention of SEQ ID NO: 49.

According to another further embodiment, is provided a variant of peptide of SEQ ID NO: 36 according to the invention.

According to another further embodiment, is provided a variant of peptide of SEQ ID NO: 17 according to the invention wherein Xaa1 is deleted.

According to another further embodiment, is provided a variant of peptide of SEQ ID NO: 17 according to the invention wherein Xaa7 is a non-natural apolar amino acid.

According to another further embodiment, is provided a variant of peptide of SEQ ID NO: 17 according to the invention wherein Xaa19 and Xaa20 are deleted.

According to another further embodiment, is provided a variant of peptide of SEQ ID NO: 17 according to the invention wherein Xaa18, Xaa19 and Xaa20 are deleted.

According to another further embodiment, is provided a variant of peptide of SEQ ID NO: 17 according to the invention wherein Xaa16 is a non-natural apolar amino acid.

According to another further embodiment, is provided a variant of peptide of SEQ ID NO: 17 according to the invention wherein Xaa17 is a non-natural apolar amino acid. According to another further embodiment, is provided a variant of peptide of SEQ ID NO: 17 according to the invention wherein Xaa16 and/or Xaa17 is a non-natural apolar amino acid selected from Table 1a or isomers thereof.

According to another further embodiment, is provided a variant of peptide of SEQ ID NO: 17 according to the invention wherein Xaa16 and/or Xaa17 is tBa.

According to another further embodiment, is provided a peptide of the invention of formula (C2).

According to another further embodiment, is provided a variant of peptide of SEQ ID NO: 36 according to the invention.

According to another further embodiment, is provided a variant of peptide of SEQ ID NO: 49.

According to another further embodiment, is provided a peptide of the invention of formula (C6).

According to another further embodiment, is provided a variant of peptide of SEQ ID NO: 36 selected from a peptide of SEQ ID NOs: 38, 39, 40, 41, 42, 43, 44, 45, 46, 47, 48 and 49.

According to another further embodiment, is provided a peptide of the invention comprising the amino acid sequence of SEQ ID NO: 1, wherein Xaa8, Xaa12, Xaa15, and Xaa19 are each independently a cross-linked amino-acid (SEQ ID NO: 33).

According to another further embodiment, is provided a peptide of the invention comprising the following amino acid sequence: Glu Lys Ile Asn Gln Ser Leu Xaa8 Phe Ile Arg Xaa12 Ser Asp Xaa15 Leu Leu His Xaa19 Val (SEQ ID NO: 34), wherein Xaa8, Xaa12, Xaa15 and Xaa19 are each independently a cross-linked amino-acid, as well as pharmaceutically acceptable salts and pharmaceutically active variants thereof.

According to another further embodiment, is provided a peptide of the invention comprising a sequence of SEQ ID NO: 33 or 34, wherein the cross-linked amino-acids are (S)-2-(4-pentenyl)alanine.

According to another further embodiment, is provided a peptide of the invention comprising a sequence of SEQ ID NO: 33 or 34, wherein the cross-linked amino-acids are (S)-2-(4-pentenyl)glycine.

According to another further embodiment, is provided a peptide of the invention of SEQ ID NO: 19, as well as pharmaceutically acceptable salts and pharmaceutically active variants thereof.

According to another further embodiment, is provided a peptide of the invention of SEQ ID NO: 50, as well as pharmaceutically acceptable salts and pharmaceutically active variants thereof.

According to another further embodiment, is provided a peptide of the invention of SEQ ID NO: 20, as well as pharmaceutically acceptable salts and pharmaceutically active variants thereof.

According to another further embodiment, is provided a peptide of the invention of formula (C4).

According to another further embodiment, is provided a peptide of the invention of formula (C5).

According to another further embodiment, is provided a peptide of the invention of formula (C7).

According to a particular embodiment, a variant of a peptide according to the invention is selected from the group consisting of: $V4bb_{497}$, $V4bb_{498}$, $V4bb_{499}$, $V4bb_{501}$, $V4bb_{502}$ $V4bb_{503}$, $V4bb_{505}$, $V4bb_{510}$, $V4bb_{512}$, $V4bb_{514}$, $V4bb_{515}$ and $V4bb_{516}$ (SEQ ID NO.: 4-6 and 8 to 16) as defined herein.

According to a particular embodiment, a variant of a peptide according to the invention is $V4a_{500}$ (SEQ NO.: 7).

According to a particular embodiment, a variant of a peptide according to the invention is $V4ca_{515}$ (SEQ NO.: 37).

According to a particular embodiment, a variant of a peptide according to the invention encompasses fragments of SEQ ID NO: 1 which can have between about 17 and about 20 amino acids. According to a further particular embodiment, a variant of a peptide according to the invention can be a fragment of SEQ ID NO: 1, wherein 1, 2, 3, 4, 5, 6 or 7 amino acid(s), for example 1, 2, 3 or 4, is (are) removed at the N or C-terminus not bearing a cross-linked bridge.

According to a further particular embodiment, a variant of a peptide according to the invention wherein Xaa1 is deleted.

According to another further particular embodiment, a variant of a peptide according to the invention wherein Xaa20 is deleted.

According to another further particular embodiment, a variant of a peptide according to the invention wherein Xaa20 and Xaa19, when not bearing a cross-linked bridge, are deleted.

According to another further particular embodiment, a variant of a peptide according to the invention wherein Xaa20 and Xaa19 and Xaa18, when not bearing a cross-linked bridge, are deleted.

According to a further particular embodiment, a variant of a peptide according to the invention wherein Xaa1, Xaa20, Xaa18 and Xaa19, when not bearing a cross-linked bridge, are deleted.

According to a particular embodiment, the cross-linked amino-acids are C-alpha alkylated, in particular methylated.

According to a particular embodiment, the cross-linked amino-acids are both C-alpha alkylated, in particular methylated and acetylated at the N-terminus.

Compositions

The invention provides pharmaceutical or therapeutic agents as compositions and methods for treating a subject, preferably a human subject who is suffering from a medical disorder, and in particular a disorder associated with RSV infection such as lower respiratory disorders.

Pharmaceutical compositions of the invention can contain one or more compound according to the invention in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably sprayable or inhalable.

Compositions of this invention may also be liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in *The Science and Practice of Pharmacy* (Remington: The Science & Practice of Pharmacy), 22$^{nd}$ Edition, 2012, Lloyd, Ed. Allen, Pharmaceutical Press, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycolate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane.

Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Alternatively, compositions of this invention may also be formulated as an aerosolable solution or an inhalable pharmaceutically acceptable composition, e.g. suitable for prevention and/or treatment of respiratory diseases. In such a formulation, the compound according to the invention is prepared for example as an inhalable dry powder or as an aerosolable solution.

Mode of Administration

Compositions of this invention may be administered/delivered in any manner including, but not limited to, orally, parenterally, sublingually, transdermally, transmucosally, topically, via inhalation, via buccal or intranasal administration, or combinations thereof. Parenteral administration includes, but is not limited to, intravenous, intra-arterial, intra-peritoneal, subcutaneous and intramuscular.

The compositions of this invention may also be administered in the form of an implant, which allows slow release of the compositions as well as a slow controlled i.v. infusion.

In another particular embodiment, a compound according to the invention is administered systemically by injection.

In another particular embodiment, a compound according to the invention is administered by inhalation or spraying.

In a specific embodiment, the method according to the invention is a method of administering a compound according to the invention to the lungs of a subject, comprising: dispersing a dry powder composition or an inhalable formulation comprising a compound according to the invention to form an aerosol; and delivering the aerosol to the lungs of the subject by inhalation of the aerosol by the subject, thereby ensuring delivery of the compound according to the invention to the lungs of the subject. Typically, the aerosol is delivered to the endobronchial space of airways from the subject.

For example, the compound according to the invention is delivered by a dry powder inhaler or by a metered dose inhaler.

This invention is further illustrated by the following examples that are not intended to limit the scope of the invention in any way.

The dosage administered, as single or multiple doses, to an individual will vary depending upon a variety of factors, including pharmacokinetic properties, subject conditions and characteristics (sex, age, body weight, health, size), extent of symptoms, concurrent treatments, frequency of treatment and the effect desired.

Combination

According to the invention, the compound can be administered alone or in combination with a co-agent useful in the prevention and/or treatment of a viral infection such as for example Synagis (Mejias et al., 2008. *Biologics*, 2 (3), 433-439) and also with the non-fusion inhibitors currently in the clinics ALX-0171 (Detalle L et al., 2017, supra) and ALS-008176 (DeVincenzo, et al., 2015, *N Engl J Med*, 373:2048-2058) or further inhibitors targeting the RSV N0-P complex (WO 2015/135925), RV568/JnJ 49095397 (protein kinase inhibitor) and ALN-RSV01.

According to a particular aspect, the compounds of the invention are administered in combination with at least one smoothened receptor (Smo) antagonist as a co-agent such as described in Bailly et al., 2016, *Scientific Reports*, 6: 25806.

According to a particular aspect, the said Smo antagonist is selected from cyclopamine or jervine.

The invention encompasses the administration of a compound of the invention wherein the compound is administered to an individual prior to, simultaneously or sequentially with other therapeutic regimens or co-agents useful in the prevention and/or treatment of respiratory diseases or disorders such as asthma and bronchiolitis (e.g. multiple drug regimens), in a therapeutically effective amount.

The invention encompasses the administration of a compound of the invention wherein the compound is administered to an individual prior to, simultaneously or sequentially with other co-agents useful in the prevention and/or treatment. The compound according to the invention that is administered simultaneously with said co-agents can be administered in the same or different compositions and in the same or different routes of administration.

Patients

In an embodiment, subjects according to the invention are patients suffering from or at risk of suffering from a disease or disorder related to a RSV infection, especially lower respiratory infections.

In another embodiment, patients according to the invention are patients suffering from severe asthma and bronchiolitis due to RSV infection.

USE ACCORDING TO THE INVENTION

The compounds according to the invention are useful in the prevention and/or treatment of a disease or a disorder related to a RSV infection, especially lower respiratory infections caused by RSV.

Within the context of this invention, the beneficial effect includes but is not limited to an attenuation, reduction, decrease or diminishing of the pathological development after onset of the disease.

In one embodiment, the invention provides a compound of SEQ ID NO: 1 or variants thereof for use according to the invention.

In another embodiment, the invention provides a compound for use according to the invention, wherein the compound is of SEQ ID NO: 2 or a variant thereof.

In another embodiment, the invention provides a compound for use according to the invention, wherein the compound is of SEQ ID NO: 3 or a variant thereof.

In another embodiment, the invention provides a compound for use according to the invention, wherein the compound is of SEQ ID NO: 17 or a variant thereof.

In another embodiment, the invention provides a compound for use according to the invention, wherein the variant is of SEQ ID NO: 4-6 or 8 to 16.

In another embodiment, the invention provides a compound for use according to the invention, wherein the compound is of SEQ ID NO: 33 or a variant thereof.

In another embodiment, the invention provides a compound for use according to the invention, wherein the variant is of SEQ ID NO: 34 or a variant thereof.

In another embodiment, the invention provides a compound for use according to the invention, wherein the variant is of SEQ ID NO: 18 or a variant thereof.

In another embodiment, the invention provides a compound for use according to the invention, wherein the compound is of SEQ ID NO: 36 or a variant thereof.

In another embodiment, the invention provides a compound for use according to the invention, wherein the variant is of SEQ ID NO: 37.

In another embodiment, the invention provides a compound for use according to the invention, wherein the variants are selected from a compound of SEQ ID NO: 38, 39, 40, 41, 42, 43, 44, 45, 46, 47, 48 and 49.

In another embodiment, the invention provides a compound for use according to the invention, wherein the variants are selected from a compound of SEQ ID NO: 38, 39, 43, 44, 45, 46, 47 and 49.

In another embodiment, the invention provides a compound for use according to the invention, wherein the compound is of SEQ ID NO: 19 or a variant thereof.

In another embodiment, the invention provides a compound for use according to the invention, wherein the compound is of SEQ ID NO: 50 or a variant thereof.

In another embodiment, the invention provides a compound for use according to the invention, wherein the variant is of SEQ ID NO: 7.

In another embodiment, the invention provides a compound for use according to the invention, wherein the compound is of SEQ ID NO: 20 or a variant thereof.

In another embodiment, the invention provides a compound for use according to the invention, wherein the compound is of Formula (C1).

In another embodiment, the invention provides a compound for use according to the invention, wherein the compound is of Formula (C2).

In another embodiment, the invention provides a compound for use according to the invention, wherein the compound is of Formula (C3).

In another embodiment, the invention provides a compound for use according to the invention, wherein the compound is of Formula (C4).

In another embodiment, the invention provides a compound for use according to the invention, wherein the compound is of Formula (C5).

In another embodiment, the invention provides a compound for use according to the invention, wherein the compound is of Formula (C6) and isomers thereof.

In another embodiment, the invention provides a compound for use according to the invention, wherein the compound is of Formula (C7).

In a further embodiment, the mammal is human, in particular a newborn or infant.

The novel derivatives according to the invention can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures.

In particular, cross-linked amino acids according to the invention can be obtained as described herein.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. The invention having been described, the following examples are presented by way of illustration, and not limitation.

EXAMPLES

The following abbreviations refer respectively to the definitions below:
FCS (Foetal Calf Serum); HCTU (2-(6-Chloro-1H-benzotriazole-1-yl)-1,1,3,3-tetramethylaminium hexafluorophosphate), TFA (trifluoroacetic acid), TIS (Triisopropylsilane).

The following commercial materials were used: Fmoc-amino acids and coupling reagents were purchased from Aapptec, Novabiochem and Bachem. The non-natural olefinic containing amino-acids were purchased at Okeanos Tech. Co., LTD. Solvents were purchased from Acros, Biosolve and Sigma-Aldrich. HEp-2 (ATCC number CCL-23) cells were maintained in Eagle's minimum essential medium (EMEM) supplemented with 10% FCS, 2 mM L-glutamine, and penicillin-streptomycin solution. The cells were grown in an incubator at 37° C. in 5% $CO_2$. Cytotoxicity assays were done with the CellTiter-Glo Luminescent cell viability assay (Promega). Cells were transfected using Lipofectamine 2000 (Invitrogen, Cergy-Pontoise, France) as described by the manufacturer.

Example 1: Synthesis of Compounds According to the Invention

The general synthetic approach for obtaining compounds of Formula (I) comprises a classical solid phase peptide synthetic process wherein non-commercial groups are first prepared separately according to standard methods before grafting.

Compounds of the invention were synthesized by solid phase peptide chemistry on a Rink Amide AM resin LL (100-200 mesh, Novabiochem) using an Apex 396 Automated Multiple Peptide Synthesizer (Aapptec) at a 50 µmol scale. Each coupling to was performed for 1 h at room temperature, using 200 µmol of Fmoc amino acid pre-activated with 190 µmol of HCTU and 400 µmol of diisopropyldiethylamine (DIEA) in N-Methyl-2-pyrrolidone (NMP). For the coupling following the non-natural olefinic amino acids ((S)-2-(4-pentenyl)alanine, (R)-2-(4pentenyl)alanine), HCTU was replaced by 200 µmol of PyClock or HATU, and the coupling was performed twice for two hours at room temperature. Following final Fmoc deprotection and N-terminal acetylation, the metathesis was performed under constant nitrogen degassing, in a 2 ml solution containing 10 mM $1^{st}$ generation Grubbs' catalyst in dichloroethane (DCE). The metathesis was performed twice for 2 hours at room temperature. Peptides were deprotected and cleaved from the resin with a cleavage cocktail consisting of TFA: TIS:$H_2O$ (95/2.5/2.5) for 1 h30. Crude peptides were analyzed by UPLC/MS (Waters Acquity Ultra Performance LC/Micromass Quattro micro API) on a ACQUITY UPLC BEH C18 column (1.7 µl, 1.0×50 mm), and purified by HPLC preparative (Waters 2777 sample manager, Waters 2545 binary gradient module, Waters 2487 Dual X Absorbance Detector) using a Waters C18 Xbridge PreShield RP18 column (19×100 mm; diam. particle size, 5 µm). Samples were lyophilized and quantified with the Qubit® 2.0 Fluorometer (Life Technologies).

The peptides of the invention were compared to comparative peptides of the same length and to the best peptide candidate (SAH-RSVF$_{BD}$), a 35-mer, reported by Bird et al., 2014, supra based on the T118 sequence (FIG. 1B, Table 3) which contains the N-terminal section of HR-2 lacking in peptide 4bb and spans three additional helical turn at the N-terminus and an unfolded area at the C-terminus of the peptide. The alpha-helical structure of SAH-RSV$_{BD}$ is stabilized with two (i, i+7) staples, while the peptides 4bb and 4ac are constrained with two (i, i+4), and (i, i+3), (i, i+4) staples, respectively (FIGS. 1B & C). Peptide 4a is constrained with the same two (i, i+4) staples, and peptide 3ac has the same sequence than peptide 4a, truncated of 4 amino-acids at its N-terminus. Peptide 4bb is a compound of Formula (C1), 4ca of Formula (C2), 4bb' of Formula (C3), 4a of Formula (C4), 3ac of Formula (C5).

Further peptides of the invention have been synthesized according to similar methods. Non-natural amino acids are introduced by standard Fmoc solid state peptide synthesis by using fmoc-protected amino acid starting material.

Peptides 4ca18, 4ca16 and 4cavar8 are variants of 4ca having respectively 18, 16 and 18 amino acids. Peptides 4cavar1, 4cavar2, 4cavar3, 4cavar4, 4cavar5, 4cavar6, 4cavar7, 4cavar8 and 4cavar9 are variants of 4ca containing non-natural apolar amino acids. Peptide 4ca2 is a variant of 4ca having different cross-linking amino acid ((S)-2-(4-pentenyl)glycine instead of (R)-2-(4-pentenyl)alanine in positions $X_{aa5}$, $X_{aa8}$, $X_{aa12}$ of SEQ ID NO: 1, 17 or 18) and peptide 4a2 is a variant of 4a having different cross-linking amino acid ((S)-2-(4-pentenyl)glycine instead of (S)-2-(4-pentenyl)alanine in positions $X_{aa8}$, $X_{aa12}$, $X_{aa15}$ and $X_{aa19}$ of SEQ ID NO: 1, 33 or 34).

SAH-RSVF$_{BD}$ was synthesized by solid phase peptide synthesis. Unexpectedly, two isomers of identical mass were identified during the analysis of the crude material, which most likely result from the formation of two isomers at the staple olefinic bond. This isomerization has not been reported by the authors. The isomers were purified and arbitrarily assigned these isomers as SAH-RSVF$_{BD}$ (Z) and RSVF$_{BD}$ (E). The identity of both isomers was confirmed by UPLC, ES-MS and amino acid analysis.

The secondary structure of the peptides was then characterized by circular dichroism (DC) as described below. The peptides sequences of peptides of the invention, including the variants of 4bb (V4bb), 4a and 4ca, and together with the comparative peptides are presented in Tables 2 and 3 from FIG. 2.

The helicities of peptides of the invention comparted to those of the comparative peptides are presented in Table 4 below.

TABLE 4

| Peptide | % helicity |
| --- | --- |
| 4bb | 52.9 |
| 4ca | >100 |
| 3 | 6.6 |
| 3a | 33.9 |
| 3ac | 47.2 |
| 4ca18 | 43 |
| 4ca16 | >100 |
| 4ca-var1 | 89.3 |
| 4ca-var2 | 90.3 |
| 4ca-var3 | 91.4 |
| 4ca-var4 | 98.4 |
| 4ca-var5 | 82.3 |
| 4ca-var6 | 85.6 |
| 4ca-var7 | 91.4 |
| 4ca-var8 | 75.8 |
| 4ca2 | 58.1 |
| 4 | 6.6 |
| 4e | 23.3 |
| 4a | 23.5 |
| 4a2 | 46 |
| 4ef | 50.7 |
| 4bf | >100 |
| 1eg | 35.3 |
| T118 | 23.4 |

As expected, stapling conferred a significant enhancement of α-helical content to all peptides as observed by the displacement of the random coil minimum toward 208 nm and the appearance of a second minimum at 222 nm (FIG. 2A). The α-helical content increased from 5.9% or 6.6%, a pattern consistent with an unstructured peptide for the non-stapled native comparative peptides 3 and 4, respectively to 33.9 or 23.3% for the single stapled comparative peptides 3a and 4e, respectively.

Double stapled comparative peptide 4a displayed an unusual strong negative Cotton effect at 222 nm in the CD spectra (FIG. 2A) suggesting that this peptide may have oligomerizing properties The CD spectra of the peptides of the invention 4bb and 3ac and comparative peptide 4ef and leg appeared to display similar negative Cotton effect at the minima of 208 nm and 222 nm, with α-helical contents in a similar range. The CD spectra of the peptide of the invention 4ca and comparative peptide 4bf showed unusual conformational properties for peptides of this size in an aqueous environment, suggesting that they are fully folded into α-helices.

Variants of peptides of the invention 4bb mutated with one alanine (SEQ ID NO: 4-5, 7 and 10-16) overall retained a helical content similar to peptide 4bb (approximately 50%), except mutants V4bb$_{501}$ (SEQ ID NO: 3 wherein $Q_5$ is replaced by A), V4bb$_{502}$ (SEQ ID NO: 3 wherein $S_6$ is replaced by A), and V4bb$_{499}$ variants (SEQ ID NO: 3 wherein $I_3$ is replaced by A), (SEQ ID NO: 8, 9 and 6) that appeared to be less α-helical 12, 15 and 24%, respectively.

A loss of inhibition was observed with SEQ ID NO: 3 wherein $I_{10}$, $R_{11}$, $K_{12}$ and $S_{13}$ are mutated by Ala was not due to a decrease of α-helical content, which remains similar. Most of the tested peptides of the invention have a helicity higher than 45%.

CD Spectroscopy

The circular dichroism spectra were acquired on a Jasco J-810 and on a Chirascan spectropolarimeter. The samples were prepared in 10 mM phosphate buffer, pH 7.5, at a peptide concentration of 50 μM. Data were recorded at 25° C. by stepscan from 180 nm to 260 nm in a 0.1 cm pathlength quartz cell using 0.2 nm wavelength increments, 1 nm bandwidth and a response time of 0.5 sec. Each spectrum was an average of three measurements and was subtracted from buffer baseline. The data were converted to per residue molar ellipticity units [θ] (deg·cm2·dmol−1·residue−1) and smoothed using the Igor software. The percentage of helicity was calculated as it follows:

$$\% \text{ Helicity} = \frac{100 * CD_{222}}{C * N * \left\{-40000 * \left[1 - \left(\frac{2.5}{N}\right)\right]\right\}} \quad (1)$$

whereby CD222=molar ellipticity [0] at 222 nm in [mdeg], N=number of amino acids in the peptide and C=peptide molar concentration [mol/l].

Example 2: Inhibitory Activity of Compounds of the Invention on Viral Fusion by Competition with HR2 Fluorescently Labeled Peptide (T108)

To assess the propensity of the peptides to inhibit viral fusion, a 5 helix-bundle (5HB) biochemical polarization competition assay that has been described previously (Park et al., 2011, Anal. Biochem., 409:195-201) is used. Briefly, each stapled peptides were assessed for their ability to compete with the binding of a HR2 fluorescently labeled peptide (T108) to 5HB, a recombinant 5 helix bundle protein (5HB) containing 3 HR1 domains covalently attached to 2 HR2 domains prepared as described below.

Variants of SEQ ID NO: 4-6, 8-16 of peptide of the invention 4bb, variant of SEQ ID NO: 7 of peptide of the invention 4a and variant of SEQ ID NO: 37 of peptide of the invention 4ca mutated with an alanine were capable to block the increase of FP in similar extent than 4bb.

Cloning, Expression and Purification of 5HB

The coding sequence of 5HB was designed as described previously and de novo synthesized by Genscript (Park et al., 2011, supra). The HR1 (126-182) and HR2 (476-524) coding sequences from wild type RSV A2 strain (Yunus et al., 2010, Virology, 396:226-23721) were codon optimized for overexpression in *E. Coli* and cloned in the NdeI/BamHI restriction sites to of pET-15b to generate the expression plasmid for 5HB. The 5HB expression construct was transformed into *Escherichia coli* BL21 (DE3). 100 ml of LB medium supplemented with ampicillin (100 µg/ml) was inoculated with 50 µl of cryopreserved transformant overnight at 37° C., the preculture was transferred to 1 liter of fresh LB medium supplemented with ampicillin to reach reached an optical density of 0.1 measured at 600 nm. Cells were grown at 37° C. to an optical density at 600 nm of 0.8 followed by induction with isopropyl-1-thio-β-D-galactopyranoside at final concentration of 0.5 mM. After overnight of induction, cells were harvested by centrifugation, washed twice with PBS and resuspended in 20 ml of PBS, pH 7.4, 500 mM NaCl and 1% Triton X-100 supplemented with complete protease inhibitor. Cell suspensions were disrupted by sonication. Cell debris was removed through ultracentrifugation at 18,000×g for 1 h at 4° C., and clarified cell lysate was mixed with 1 ml of Ni-NTA agarose beads (QIAGEN) pre-equilibrated with 20 ml of lysis buffer. The suspension was agitated for one hour at 4° C. and loaded onto a 5 ml polypropylene column (QIAGEN). The column was washed twice with 8 ml of PBS, pH 7.4, 500 mM NaCl, 1% Triton X-100 and 100 mM imidazole. Proteins were eluted with 5×500 µl of a buffer containing PBS, pH 7.4, 300 mM imidazole and 500 mM NaCl. The imidazole was removed by dialysis, and protein purity was assessed SDS polyacrylamide gel electrophoresis on Nu-PAGE precast gels (Invitrogen, Carlsbad, Calif.). Protein concentration was determined with the Qubit® 2.0 Fluorometer (Life Technologies).

5HB Fluorescence Polarization Assay

The T108 peptide probe was synthesized by standard SPPS procedures using HCTU as a coupling reagent as described above. The fluorescence polarization assay was performed in 384-well plates using a Spectramax Paradigm (Molecular devices), using an excitation and emission wavelength of 485 nm and 535 nm, respectively. The acquisition time was of 700 ms and the read height was of 1 mm. 10 µL of recombinant 5HB protein in FP buffer (20 mM PBS, pH 7.4, 500 mM NaCl, 0.01% [v/v] Tween 20, and 0.05 mg/ml bovine gamma globulin, was preincubated for 10 minutes at room temperature with 10 µL of the appropriate peptide inhibitor concentration, after which 10 µL of FITC-T108 was added and further incubated for 30 min. at rt. The final concentration of protein and probe was of 50 nM and 2 nM, respectively. All experiments were performed in duplicate. The percentage of inhibition was calculated as described (Park et al., 2011, supra), and the $K_D$ value was calculated with the Igor software.

Example 3: Inhibitory Activity of Compounds of the Invention on Cellular Viral Fusion The inhibitory activity of the peptides of the invention was assessed in a cellular viral fusion assay as compared to comparative peptides as follows. A549 cells were infected with a recombinant green fluorescent protein (GFP)-expressing RSV virus (strain A2) obtained as described below and in Hallak et al., 2000, *Virology*, 271:264-275, and the inhibitory activity of the peptides was quantified by flow cytometry.

Peptide of the invention 3ac was capable to block viral infection of cells with an $EC_{50}$ value of 15.3±5.9 µM, similarly to T108. Under those conditions, T108 was significantly less potent ($EC_{50}$=20.9 µM) than reported previously ($EC_{50}$=1.48 µM) (Lambert et al., 1996, supra). The single stapled comparative peptides 3a and 4e were inactive in the cellular assay ($EC_{50}$>90 µM for both peptides) despite of at least 20% of α-helical content and reasonable activity in the biochemical 5HB assay above.

Peptide 4a was slightly more potent than peptide 3ac in the cellular viral fusion assay ($EC_{50}$=10.6 µM versus $EC_{50}$=15.3 µM, respectively) and peptides of the invention 4bb and 4ca were more clearly potent inhibitors ($EC_{50}$=2.27 µM and $EC_{50}$=4.08 µM, respectively) than comparative peptide 4a. Comparative peptides 4ef and 4bf were inactive in cellular settings.

Variants of SEQ ID NO: 4-6, 8-16 of peptide of the invention 4bb mutated with an alanine had a similar activity as 4bb.

Inhibitory activity of SAH-RSVF$_{BD}$ (Z) and (E) were similar to the activities of peptides 4bb and 4ca.

These findings indicates that high helical contents do not necessarily parallel antiviral potencies as shown by comparative peptides 4bf and 4ef showing high helical content and low or lack of potency as compared to peptides of the invention.

Further, the lower activity of peptides 4bf and 4ef also indicate that stapling at the non-interacting face of the helix of the HR-2 domain (i.e. residues E497, K498, N500, Q501, L503, A504, F505, R507, K508, D510, E511, L512, H514 and N515) will not necessarily result in conservatively active peptides, as opposed to what was previously believed (Bird et al., 2014, supra). Finally, improved activity of peptides of the invention as compared to peptides 4bf and 4ef is also unexpected in view of the earlier disclosed advantages of i, i+7 staples over i, i+4 (Bird et al., 2014, supra).

HRSV-eGFP Inhibition Assay

Following rapid thawing of the frozen eGFP encoding RSV virus at 370° C., the virus was vortexed for 2 min, and pipetted up and down to break aggregates. Serial 4-fold dilutions of inhibitors were prepared in glass tubes and mixed with a volume of virus required to achieve approximately 50% of infection in 200 µl of media containing 2% of FCS. The resulting mixture was added to 24-well plates containing A549 cells. Cells were incubated for 2 hours at 37° C., the media was replaced, and cells were incubated for an additional 24 hours. Cells were treated with 300 µl of trypsin for 10 min at 37° C., and the detached cells were diluted in 1 ml of culture medium. Following centrifugation at 1'700 rpm, the pellet was resuspended in 300 µl of PBS+1% SBF (V/V) and GFP positive cells were counted by FACS analysis.

Example 4: Inhibitory Activity of Peptides of the Invention in HEp-2 Cells

The inhibitory activity of the peptides of the invention was assessed in HEp-2 cells as described below:

A mCherry-expressing virus recently developed (Rameix-Welti et al., 2014, *Nat. Commun.*, 5:5104) was used to avoid the cumbersome manipulations required with the GFP-expressing virus. Under these assay conditions peptides of the invention 4a, 4ca, 4bb and 4bb' show clear higher activities as compared to comparative peptides T118, 4ef, 4bf (Table 5). In particular, the comparative single stapled peptides 3a and 3c were inactive. The finding that peptide 4bb' is almost as active than its parent peptide 4bb, shows that the alpha-methyl moiety of the non-natural amino acids used for the stapling is not required to successfully inhibit viral fusion.

TABLE 5

| Peptide | EC$_{50}$ values [μM] Average |
|---|---|
| 4ca | 0.59 ± 0.13 |
| 4bb | 0.74 ± 0.27 |
| T118 | 6.33 ± 1.49 |
| 4ef | 3.07 ± 1.45 |
| 4bf | 2.49 ± 0.09 |
| 4a | 1.82 ± .0.42 |
| 4ca18 | 0.23 ± 0.03 |
| 4ca16 | 0.72 ± 0.06 |
| 4ca-var1 | 1.36 ± 0.19 |
| 4ca-var2 | 1.49 ± 0.14 |
| 4ca-var3 | 0.77 ± 0.08 |
| 4ca-var4 | 0.20 ± 0.05 |
| 4ca-var5 | 0.85 ± 0.08 |
| 4ca-var6 | 2.31 ± 0.44 |
| 4ca-var7 | 0.231 ± 0.03 |
| 4ca-var8 | 1.32 ± 0.08 |
| 4ca-var9 | 1.89 ± 0.32 |
| 4ca2 | 0.33 ± 0.05 |
| 1b | >25 |
| 3a | >25 |
| 3c | >25 |
| 3f | 51.26 ± 5.24 |
| 4bb' | 0.99 |

These data show that the presence of two staples in peptide of the invention such as 4ca, 4bb, 4bb' and 4a unexpectedly resulted in an increase of antiviral potency of 11-, 9-, 6- and 3-fold, respectively, despite the reduction of size from 35 amino acids in T118 to 20 amino acids. Likewise, the double stapled peptides 4ca and 4bb displayed an inhibitory activity similar to the double stapled peptide SAH-RSVBD (Z) and (E) that also contain 35 amino acids. 4bb' is a 4bb variant as described in FIG. 2 with stapling using pentenyl glycine instead of pentenyl alanine (no methyl group at the C-α moiety of the non-natural amino acid used for the stapling).

rHRSV-mCherry Inhibition Assay

HEp-2 cells were seeded at 5×104 cells per well in 96 wells plate the day before the infection. Peptides were 2-fold serially diluted in DMSO (11 dilutions), then further diluted in MEM medium and pre-incubated for 15-20 minutes with 0.2 MOI of RSV-mCherry (Rameix-Welti et al., 2014, supra). Following the washing of Hep-2 cells with MEM without phenol red medium, the cells were incubated with the virus/peptide mixtures for a period of 1 h30-2 h. The cells were washed and further incubated in MEM media containing fetal bovine serum and the same concentration of peptide that was used during the infection step. Plates were incubated 48 h at 37° C. and the mCherry fluorescence was measured using a spectrofluorometer (Tecan infinite M200PRO) with excitation and emission wavelengths of 580 and 620 nm, respectively (expressed in relative fluorescence units RFU). Non-infected HEp-2 cells were used as standards for fluorescence background levels. Each experiment was performed in duplicate and repeated at least twice.

Example 5: Stability of the Compounds of the Invention after Treatment with Proteases The compounds according to the invention are tested for their stability in a proteolytic stability assay as described below which is an important parameter to assess for the development of peptide therapeutics. Peptides of the invention 4bb, 4ca, 4a and their unstapled comparative peptide 4, as well as both SAH-RSVF$_{BD}$ isomers were treated with chymotrypsin and trypsin, and analysed by LC/MS to quantify the reaction products over time. As expected, all stapled peptides were significantly more stable to proteolytic degradation than the native peptide 4, which is fully degraded in 10 min (Table 6).

TABLE 6

| Peptide | t$_{1/2}$ (min) Chymotrypsin | t$_{1/2}$ (min) Trypsin |
|---|---|---|
| 4 | 4.5 | 5 |
| 4a | 4481.5 | 76 |
| 4bb | 3008.0 | 20 |
| 4ca | 10'795.0 | 2'277 |
| RSV-SAH$_{BD}$ (Z) | 442.1 | 5 |
| RSV-SAH$_{BD}$ (E) | 391.3 | 1 |

Figure 3:
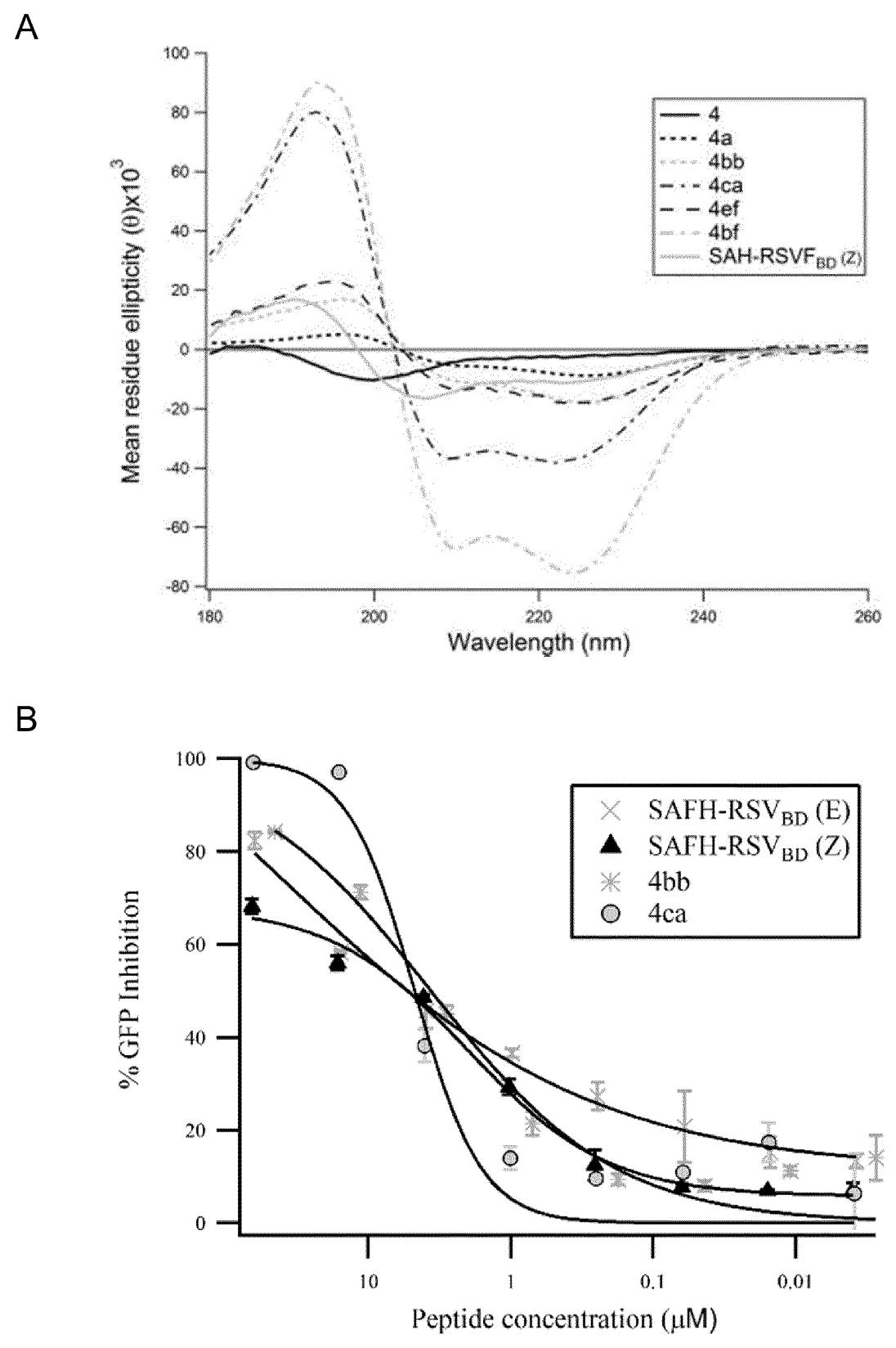

As it can be seen in FIG. 3C, peptides of the invention are highly resistant to proteolytic stability, particularly peptide 4ca, which displayed a half-life of 180 and 38 hrs against chymotrypsin and trypsin, respectively. In comparison, both SAH-RSVF$_{BD}$ isomers were more susceptible to proteolytic degradation with half-life of approximately 7 hours and 5 min against chymotrypsin and trypsin, respectively. Altogether, those results show that remarkably, peptides of the invention retain high inhibitory activity, unexpectedly given that these peptides interact with a smaller surface area on the trimeric HR1 target protein and are less susceptible to chymotrypsin and trypsin degradation. Further, this is even more surprising since the retaining of the activity does not necessarily parallel alpha helical contents and shortening of the native peptide does not necessarily preserve the activity.

Proteolytic Stability Assay

In vitro proteolytic degradation was measured via LC-MS using an Agilent Infinity 1280 UHPLC system coupled to an Agilent quadruple-time-of-flight (QTOF) 6530 with an Agilent Jet Stream electrospray ionisation (AJS ESI) source (all Agilent Technologies, Waldbronn, Germany). 5 μl of digested sample were injected onto a C18 column (Zorbax Eclipse Plus RRHD, 1.8 μm, 2.1*100 mm, Agilent Technologies, Waldbronn, Germany) equilibrated with solvent A and eluted with a flow rate of 0.4 ml/min over a 5-95% gradient of solvent B in 5 minutes, followed by 1.5 minutes at 95% and 0.5 minutes post-time where solvent A was 95% water, 5% acetonitrile with 0.2% formic acid and solvent B was 5% water, 95% acetonitrile with 0.2% formic acid. The AJS ESI source was operated with a capillary voltage of 4000V and a nozzle voltage of 600V with a drying gas temperature of 325° C. and flow rate of 10 l/min, nebulising gas pressure of 20 psi, and a sheath gas temperature of 300° C. and flow rate of 11l/min. Mass spectra were acquired in the positive ion mode from 100-3200 m/z at a rate of 1 scan per second in extended dynamic range (2 GHz) mode. The fragmentor, skimmer and octopole Radio Frequency voltages were set to 200, 60 and 750 V respectively. Data were acquired and analysed with Agilent MassHunter Workstation (version B.05).

Peptide digestion was performed as it follows: 10 μl of peptide at 0.29 mM in 50/50 acetonitrile/water were dissolved in 990 μl 100 mM Tris-HCl, pH 8.0 with 10 mM CaCl$_2$. Following measurement of the undigested (t0) sample, 10 μl of chymotrypsin at 50 μg/ml in 100 mM Tris-HCl, pH 8.0 with 10 mM CaCl$_2$ were added and the sample was vortexed and placed immediately in the autosampler, set to 25° C. Trypsin digestion was performed as with chymotrypsin except that the buffer was in 50 mM Tris-HCl, pH8. Chymotrypsin and trypsin were purchased from Thermo Fisher Scientific.

The level of intact peptide was quantified by serial injection over time. Integration of the intact peptide compound chromatogram was performed using the Agilent Molecular Feature Extraction (MFE) algorithm. A plot of the intact peptide MFE peak area over time gave an exponential decay curve, from which the half-life was determined using MatLab (Matrix Science).

Example 6: In Vivo Activity of Peptide of the Invention in a Mice Luciferase Assay The efficacy of peptides of the invention is tested in the following model of rHRSV infection.

Female BALB/c mice around 8 weeks of age are purchased. Mice are bred in a pathogen-free animal facility. For infection experiments, mice will be housed in cages inside stainless steel isolation cabinets that are ventilated under negative pressure with high-efficiency particulate air-filtered air. Female BALB/c mice (n=5 per group) are anesthetized by a mixture of ketamine and xylazine (1 and 0.2 mg per mouse, respectively) and infected by intranasal inoculation with 50 μl of PBS containing $6.10^4$ p.f.u. of rHRSV-Luc (Luc-encoding virus that enables direct visualization of RSV replication in living mice). Peptides of the invention are administered intranasally to the mice infected or uninfected with RSV-Luc, on day 0, 2 and 4 post-infection. Body weight and temperature is monitored at days 3-10. In vivo imaging is performed each two days on anesthetized mice. At day 8, mice are killed and the safety of the treatment is investigated by a complete toxicopathological evaluation of treated mice (histologic analysis of lungs with sections of each lobe, turbinates, heart, spleen, liver, kidneys).

At day 7 pi, a time corresponding to the end of the infection in mice, the animals were sacrificed and the lungs were collected in order to perform a histological analysis. The aim of this histological analysis was to validate indirectly the efficiency of peptide 4ca by the observation of the clinical hallmarks of RSV infection. Additionally, potential toxicity of peptide 4ca due to the treatment at the tissue scale, and the potential immune response induced upon treatment was investigated. No histological changes were noticed in the lung parenchyma between mock and 4ca inoculated animals, suggesting to the absence of toxicity of 4ca in the lungs. Infection by RSV was responsible for a multifocal extensive marked interstitial pneumonia characterized by a diffuse thickening of the alveolar walls, by mononuclear cell infiltration, and by a BALT hyperplasia. In contrast, no interstitial pneumonia was observed after infection by RSV upon inoculation of 4ca, although some BALT hyperplasia and the presence of some degenerating cells inside the bronchial epithelium were observed. These observations confirm the antiviral effect of peptide 4ca.

SEQUENCE LISTING (Consensus)
SEQ ID No: 1
$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ wherein Xaa1, Xaa6, Xaa14 and Xaa18 are independently selected from any amino acid; Xaa2, Xaa4, Xaa5 and Xaa19 are independently selected from any amino acid or a cross-linked amino-acid; Xaa3, Xaa7, Xaa9, Xaa10, Xaa16, Xaa17 and Xaa20 are an independently selected apolar amino acid; Xaa8 is a cross-linked amino-acid; Xaa11 and Xaa12 are independently selected from a polar amino acid and a cross-linked amino-acid; Xaa13 is Serine; Xaa15 is selected from a polar amino acid and a cross-linked amino-acid; wherein the peptide contains a total of two cross-linking bridges, each between two cross-linked amino acids spaced by 2 or three amino-acids (i, i+3 and/or i, i+4 staples).

(Consensus for 4bb)
SEQ ID No: 2
$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Xaa_{18}$ $Xaa_{19}$ $Xaa_{20}$ wherein $Xaa_1$, $Xaa_2$, Xaa5, Xaa6, Xaa14, Xaa18 and Xaa19 are independently selected from any amino acid; Xaa3, Xaa7, Xaa9, Xaa10, Xaa16, Xaa17 and Xaa20 are an independently selected apolar amino acid; $Xaa_4$, $Xaa_8$, $Xaa_{11}$ and $Xaa_{15}$ are a cross-linked amino-acid; Xaa12 are independently selected from a polar amino acid; Xaa13 is Serine; wherein the peptide contains a total of two cross-linking bridges, each between two cross-linked amino acids spaced by 2 or three amino-acids (i, i+3 and/or i, i+4 staples).

(4bb specific varied on staples)
SEQ ID No: 3
EKI $Xaa_4$ QSL $Xaa_8$ FI $Xaa_{11}$ KSD $Xaa_{15}$ LLHNV wherein $Xaa_4$, $Xaa_8$, $Xaa_{11}$ and $Xaa_{15}$ are a cross-linked amino-acid.

(4bb varied with E1/A1) V4bb497
SEQ ID No: 4
<u>A</u>KI $Xaa_4$ QSL $Xaa_8$ FI $Xaa_{11}$ KSD $Xaa_{15}$ LLHNV wherein $Xaa_4$, $Xaa_8$, $Xaa_{11}$ and $Xaa_{15}$ are (S)-2-(4-pentenyl) alanine.

(4bb varied with K2/A2) V4bb498
SEQ ID No: 5
E<u>A</u>I $Xaa_4$ QSL $Xaa_8$ FI $Xaa_{11}$ KSD $Xaa_{15}$ LLHNV wherein $Xaa_4$, $Xaa_8$, $Xaa_{11}$ and $Xaa_{15}$ are (S)-2-(4-pentenyl) alanine.

(4bb varied with I3/A3) V4bb499
SEQ ID No: 6
EK<u>A</u> $Xaa_4$ QSL $Xaa_8$ FI $Xaa_{11}$ KSD $Xaa_{15}$ LLHNV wherein $Xaa_4$, $Xaa_8$, $Xaa_{11}$ and $Xaa_{15}$ are (S)-2-(4-pentenyl) alanine.

(4a varied with N4/A4) V4a500
SEQ ID No: 7
EKI <u>A</u> QSL $Xaa_8$ F I R $Xaa_{12}$ SD $Xaa_{15}$ LLH $Xaa_{19}$ V (4bb varied with Q5/A5) V4bb501
SEQ ID No: 8
EKI $Xaa_4$ <u>A</u> SL $Xaa_8$ FI $Xaa_{11}$ KSD $Xaa_{15}$ LLHNV wherein $Xaa_4$, $Xaa_8$, $Xaa_{11}$ and $Xaa_{15}$ are (S)-2-(4-pentenyl) alanine.

(4bb varied with S6/A6) V4bb502
SEQ ID No: 9
EKI Xaa₄ Q A L Xaa₈ FI Xaa₁₁ KSD Xaa₁₅ LLHNV wherein Xaa₄, Xaa₈, Xaa₁₁ and Xaa₁₅ are (S)-2-(4-pentenyl) alanine.

(4bb varied with L7/A7) V4bb503
SEQ ID No: 10
EKI Xaa₄ QS A Xaa₈ FI Xaa₁₁ KSD Xaa₁₅ LLHNV wherein Xaa₄, Xaa₈, Xaa₁₁ and Xaa₁₅ are (S)-2-(4-pentenyl).

(4bb varied with F9/A9) V4bb505
SEQ ID No: 11
EKI Xaa₄ QSL Xaa₈ A I Xaa₁₁ KSD Xaa₁₅ LLHNV wherein Xaa₄, Xaa₈, Xaa₁₁ and Xaa₁₅ are (S)-2-(4-pentenyl) alanine.

(4bb varied with D14/A14) V4bb510
SEQ ID No: 12
EKI Xaa₄ QSL Xaa₈ FI Xaa₁₁ KS A Xaa₁₅ LLHNV wherein Xaa₄, Xaa₈, Xaa₁₁ and Xaa₁₅ are (S)-2-(4-pentenyl) alanine.

(4bb varied with L16/A16) V4bb512
SEQ ID No: 13
EKI Xaa₄ QSL Xaa₈ FI Xaa₁₁ KSD Xaa₁₅ A LHNV wherein Xaa₄, Xaa₈, Xaa₁₁ and Xaa₁₅ are (S)-2-(4-pentenyl) alanine.

(4bb varied with H18/A18) V4bb514
SEQ ID No: 14
EKI Xaa₄ QSL Xaa₈ FI Xaa₁₁ KSD Xaa₁₅ LL A NV wherein Xaa₄, Xaa₈, Xaa₁₁ and Xaa₁₅ are (S)-2-(4-pentenyl) alanine.

(4bb varied with N19/A19) V4bb515
SEQ ID No: 15
EKI Xaa₄ QSL Xaa₈ FI Xaa₁₁ KSD Xaa₁₅ LLH A V wherein Xaa₄, Xaa₈, Xaa₁₁ and Xaa₁₅ are (S)-2-(4-pentenyl) alanine.

(4bb varied with V20/A20) V4bb516
SEQ ID No: 16
EKI Xaa₄ QSL Xaa₈ FI Xaa₁₁ KSD Xaa₁₅ LLHN A wherein Xaa₄, Xaa₈, Xaa₁₁ and Xaa₁₅ are (S)-2-(4-pentenyl) alanine.

(Consensus for 4ca)
SEQ ID No: 17
Xaa₁ Xaa₂ Xaa₃ Xaa₄ Xaa₅ Xaa₆ Xaa₇ Xaa₈ Xaa₉ Xaa₁₀
Xaa₁₁ Xaa₁₂ Xaa₁₃ Xaa₁₄ Xaa₁₅ Xaa₁₆ Xaa₁₇ Xaa₁₈
Xaa₁₉ Xaa₂₀ wherein Xaa1, Xaa4, Xaa6, Xaa14, Xaa18 and Xaa19 are independently selected from any amino acid; Xaa3, Xaa7, Xaa9, Xaa10, Xaa16, Xaa17 and Xaa20 are an independently selected apolar amino acid; Xaa₂, Xaa₅, Xaa₈ and Xaa₁₂ are independently selected from a cross-linked amino-acid; Xaa11 and Xaa15 are independently selected from a polar amino acid; Xaa13 is Serine; wherein the peptide contains a total of two cross-linking bridges, each between two cross-linked amino acids spaced by 2 or three amino-acids (i, i+3 and/or i, i+4 staples).

(4ca specific varied on staples)
SEQ ID No: 18
E Xaa₂ IN Xaa₅ SL Xaa₈ FIR Xaa₁₂ SDELLHNV wherein Xaa₂, Xaa₅, Xaa₈ and Xaa₁₂ are independently selected from a cross-linked amino-acid.

(4a)
SEQ ID No: 19
EKINQSL Xaa₈ FIR Xaa₁₂ SD Xaa₁₅ LLH Xaa₁₉ V wherein Xaa₈, Xaa₁₂, Xaa₁₅ and Xaa₁₉ are (S)-2-(4-pentenyl)alanine.

(3ac)
SEQ ID No: 20
EQSL X₅₀₄ FIR X₅₀₈ SD X₅₁₁ LLH X₅₁₅ V wherein X₅₀₄, X₅₀₈, X₅₁₁ and X₅₁₅ are (S)-2-(4-pentenyl) alanine.

(comparative peptide (4bf))
SEQ ID No: 21
EKI X₅₀₀ QSL X₅₀₄ FIR 8₅₀₈ SDELLH X₅₁₅V wherein X₅₀₀ X₅₀₄ and X₅₁₅ are (S)-2-(4-pentenyl)alanine, 8₅₀₈ is (R)-2-(7-octenyl)alanine.

(comparative peptide (4))
SEQ ID No: 22
EKINQSLAFIRKSDELLHNV (comparative peptide (4e))
SEQ ID No: 23
EKINQSL 8₅₀₄ FIRKSD X₅₁₁ LLHNV 8₅₀₄ is (R)-2-(7-octenyl)alanine, X₅₁₁ is (S)-2-(4-pentenyl)alanine.

(HR2-fragment 476-524)
SEQ ID No: 24
NFYDPLVFPSDEFDASISQVNEKINQSLAFIRKSDELLHNVNAGKSTTN (X-ray of fragment 480-516)
SEQ ID No: 25
PLVFPSDEFDASISQVNEKINQSLAFIRKSDELLHNV (T108 fragment 478-512)
SEQ ID No: 26
YDPLVFPSDEFDASISQVNEKINQSLAFIRKSDEL (T118 fragment 488-522)
SEQ ID No: 27
FDASISQVNEKINQSLAFIRKSDELLHNVNAGKST (SAH-RSVFBD)
SEQ ID No: 28
FD 8₄₉₀ SISQVN X₄₉₇ KINQSLAFI 8₅₀₇ KSDELLX₅₁₄ NVNAGKST wherein 8₄₉₀ and 8₅₀₇ are is (R)-2-(7-octenyl)alanine, X₄₉₇ and X₅₁₄ are (S)-2-(4-pentenyl)alanine.

(comparative peptide (leg))
SEQ ID No: 29
EFPS X$_{486}$ EFD X$_{490}$ SI X$_{493}$ QVN X$_{497}$ KIN wherein X$_{486}$, X$_{490}$, X$_{493}$ and X$_{497}$ are (S)-2-(4-pentenyl) alanine.

(comparative peptide (4ef))
SEQ ID No: 30
8$_{497}$ KINQSL X$_{504}$ FIR 8$_{508}$ SDELLH X$_{515}$ V wherein 8$_{497}$ and 8$_{508}$ are (R)-2-(7-octenyl)alanine, X$_{504}$ and X$_{515}$ are (S)-2-(4-pentenyl)alanine.

(comparative peptide (3))
SEQ ID No: 31
EQSLAFIRKSDELLHNV (comparative peptide (3a))
SEQ ID No: 32
EQSL X$_{504}$ FIR X$_{508}$ SDELLHNV wherein X$_{504}$ and X$_{508}$ are (S)-2-(4-pentenyl)alanine.

(Consensus for 4a)
SEQ ID No: 33
Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Xaa$_{18}$ Xaa$_{19}$ Xaa$_{20}$ wherein Xaa1, Xaa2, Xaa4, Xaa5, Xaa6, Xaa14 and Xaa18 are independently selected from any amino acid;
Xaa8, Xaa12, Xaa15, and Xaa19 are each independently a cross-linked amino-acid.
Xaa3, Xaa7, Xaa9, Xaa10, Xaa16, Xaa17 and Xaa20 are an independently selected apolar amino acid; Xaa11 is a polar amino acid; Xaa13 is Serine; wherein the peptide contains a total of two cross-linking bridges, each between two cross-linked amino acids spaced by 2 or three amino-acids (i, i+3 and/or i, i+4 staples).

(4a specific varied on staples)
SEQ ID No: 34
EKINQSL X$_{aa8}$ FIR Xaa$_{12}$ SD Xaa$_{15}$ LLH Xaa$_{19}$ V wherein Xaa8, Xaa12, Xaa15 and Xaa19 are a cross-linked amino-acid.

(4bb)
SEQ ID No: 35
EKI Xaa$_4$ QSL Xaa$_8$ FI Xaa$_{11}$ KSD Xaa$_{15}$ LLHNV wherein Xaa$_4$, Xaa$_8$, Xaa$_{11}$ and Xaa$_{15}$ are (S)-2-(4-pentenyl) alanine.

(4ca)
SEQ ID No: 36
E Xaa$_2$ IN Xaa$_5$ SL Xaa$_8$ FIR Xaa$_{12}$ SDELLHNV wherein Xaa$_2$ is (R)-2-(4-pentenyl)alanine and Xaa$_5$, Xaa$_8$ and Xaa$_{12}$ are (S)-2-(4-pentenyl)alanine.

(4ca varied with E15/A15) V4ca511
SEQ ID No: 37
E Xaa$_2$ IN Xaa$_5$ SL Xaa$_8$ FIR Xaa$_{12}$ SD<u>A</u>LLHNV wherein Xaa$_2$ is (R)-2-(4-pentenyl)alanine and Xaa$_5$, Xaa$_8$ and Xaa$_{12}$ are (S)-2-(4-pentenyl)alanine.

Peptides of SEQ ID NO: 4-16, 19-21, 23, 28-30, 32, 35, 36 and 37 have their N-terminus acetylated and their C-terminus amidated.

(4ca18)
SEQ ID No: 38
E Xaa$_2$ IN Xaa$_5$ SL Xaa$_8$ FIR Xaa$_{12}$ SDELLH wherein Xaa$_2$ is (R)-2-(4-pentenyl)alanine and Xaa$_5$, Xaa$_8$ and Xaa$_{12}$ are (S)-2-(4-pentenyl)alanine.

(4ca16)
SEQ ID No: 39
X$_{498}$ IN X$_{501}$ SL X$_{504}$ FIR X$_{508}$ SDELL wherein X$_{498}$ is (R)-2-(4-pentenyl)alanine and X$_{501}$, X$_{504}$ and X$_{508}$ are (S)-2-(4-pentenyl)alanine.

(4ca-var1)
SEQ ID No: 40
E Xaa$_2$ IN Xaa$_5$ S Xaa$_7$ Xaa$_8$ FIR Xaa$_{12}$ SDELLHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_7$ is tBa.

(4ca-var2)
SEQ ID No: 41
E Xaa$_2$ IN Xaa$_5$ S Xaa$_7$ Xaa$_8$ FIR Xaa$_{12}$ SDELLHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_7$ is Cpg.

(4ca-var3)
SEQ ID No: 42
E Xaa$_2$ IN Xaa$_5$ S Xaa$_7$ Xaa$_8$ FIR Xaa$_{12}$ SDELLHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_7$ is Chg.

(4ca-var4)
SEQ ID No: 43
E Xaa$_2$ IN Xaa$_5$ SL Xaa$_8$ FIR Xaa$_{12}$ SDE Xaa$_{16}$LHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_{16}$ is tBa.

(4ca-var5)
SEQ ID No: 44
E Xaa$_2$ I<u>K</u> Xaa$_5$ SL Xaa$_8$ FIR Xaa$_{12}$ SDE Xaa$_{16}$LHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_{16}$ is tBa.

(4ca-var6)
SEQ ID No: 45
E Xaa$_2$ I<u>R</u> Xaa$_5$ SL Xaa$_8$ FIR Xaa$_{12}$ SDE Xaa$_{16}$LHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_{16}$ is tBa.

(4ca-var7)
SEQ ID No: 46
E Xaa$_2$ IN Xaa$_5$ SL Xaa$_8$ FIR Xaa$_{12}$ SDE Xaa$_{16}$LHNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_{16}$ is Cha.

(4ca-var8)

SEQ ID No: 47

E Xaa$_2$ IN Xaa$_5$ SL Xaa$_8$ FIR Xaa$_{12}$ SDE Xaa$_{16}$LH wherein Xaa$_2$ is (R)-2-(4-pentenyl)alanine, Xaa$_5$, Xaa$_8$ and Xaa$_{12}$ are (S)-2-(4-pentenyl)alanine and Xaa$_{16}$ is tBa.

(4ca-var9)

SEQ ID No: 48

E Xaa$_2$ IN Xaa$_5$ SL Xaa$_8$ FIR Xaa$_{12}$ SDE Xaa$_{16}$

Xaa$_{17}$HNV wherein Xaa$_2$ is (R)-2-(4-pentenyl)alanine, Xaa$_5$, Xaa$_8$ and Xaa$_{12}$ are (S)-2-(4-pentenyl)alanine and Xaa$_{16}$ and Xaa$_{17}$ are tBa.

(4ca2)

SEQ ID No: 49

E Xaa$_2$ IN Xaa$_5$ SL Xaa$_8$ FIR Xaa$_{12}$ SDELLHNV wherein Xaa$_2$ is (R)-2-(4-pentenyl)alanine and Xaa$_5$, Xaa$_8$ and Xaa$_{12}$ are (S)-2-(4-pentenyl)glycine.

(4a2)

SEQ ID No: 50

EKINQSL Xaa$_8$ FIR Xaa$_{12}$ SD Xaa$_{15}$ LLH Xaa$_{19}$ V wherein Xaa$_8$, Xaa$_{12}$, Xaa$_{15}$ and Xaa$_{19}$ are (S)-2-(4-pentenyl)glycine.

Peptides of SEQ ID NO: 38-50 have their N-terminus acetylated and their C-terminus amidated.

---

The invention claimed is:

1. A compound selected from the group consisting of SEQ ID NOs: 36, 37, 38, 39, 40, 41, 42, 43, 44, 45, 46, 47, 48, and 49.

2. The compound according to claim 1, wherein said compound is SEQ ID NO: 36 or 37.

3. The compound according to claim 1, wherein said compound is SEQ ID NO: 38 or 39.

4. The compound according to claim 1, wherein said compound is SEQ ID NO: 40 or 41.

5. The compound according to claim 1, wherein said compound is SEQ ID NO: 42 or 43.

6. The compound according to claim 1, wherein said compound is SEQ ID NO: 44 or 45.

7. The compound according to claim 1, wherein said compound is SEQ ID NO: 46 or 47.

8. The compound according to claim 1, wherein said compound is SEQ ID NO: 48 or 49.

9. A pharmaceutical composition comprising at least one compound according to claim 1.

10. The pharmaceutical composition according to claim 9, wherein the composition further comprises at least one agent useful for the treatment of viral infections.

11. A method for reducing the likelihood of RSV infection or treating a subject suffering from a RSV infection comprising administering at least one compound according to claim 1 or a pharmaceutical formulation thereof to a subject in need thereof.

12. The method according to claim 11, wherein said RSV infection is lower respiratory infection caused by RSV.

13. The method according to claim 11, wherein said at least one compound is SEQ ID NO: 46.

\* \* \* \* \*

UNITED STATES PATENT AND TRADEMARK OFFICE
CERTIFICATE OF CORRECTION

PATENT NO. : 11,299,518 B2
APPLICATION NO. : 16/081431
DATED : April 12, 2022
INVENTOR(S) : O. Nyanguile et al.

It is certified that error appears in the above-identified patent and that said Letters Patent is hereby corrected as shown below:

In the Specification

Column 3,
Line 57, "T1118" should read --T118--.

Column 11,
Line 62, "Asn Gin Ser" should read --Asn Gln Ser--.

Column 12,
Line 37, "V4ca$_{515}$" should read --V4ca$_{511}$--.

Column 18,
Line 20, "coupling to was performed" should read --coupling was performed--.
Lines 40-41, "Dual X Absorbance" should read --Dual λ Absorbance--.

Column 24,
Line 60, "(to)" should read --(t$_0$)--.

Column 25,
Line 43, "suggesting to the absence" should read --suggesting the absence--.

Column 26,
Lines 59-63,
"EKI A QSL Xaa$_8$ F I R Xaa$_{12}$ SD Xaa$_{15}$ LLH Xaa$_{19}$ V
(4bb varied with Q5/A5) V4bb501" should read
--EKI A QSL Xaa$_8$ F I R Xaa$_{12}$ SD Xaa$_{15}$ LLH Xaa$_{19}$ V
Xaa$_8$, Xaa$_{12}$, Xaa$_{15}$ and Xaa$_{19}$ are (S)-2-(4-pentenyl)alanine.
(4bb varied with Q5/A5) V4bb501--.

Signed and Sealed this
Seventeenth Day of October, 2023

*Katherine Kelly Vidal*
Katherine Kelly Vidal
*Director of the United States Patent and Trademark Office*